(12) United States Patent
Stearns et al.

(10) Patent No.: US 10,775,308 B2
(45) Date of Patent: Sep. 15, 2020

(54) APPARATUS AND METHODS FOR DETERMINING OPTICAL TISSUE PROPERTIES

(75) Inventors: Daniel G. Stearns, Los Altos, CA (US); Bradley W. Rice, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 1125 days.

(21) Appl. No.: 11/844,551

(22) Filed: Aug. 24, 2007

(65) Prior Publication Data
US 2008/0052052 A1 Feb. 28, 2008

Related U.S. Application Data

(60) Provisional application No. 60/840,247, filed on Aug. 24, 2006.

(51) Int. Cl.
*G01N 21/64* (2006.01)
*A61B 5/00* (2006.01)
*G01N 21/47* (2006.01)

(52) U.S. Cl.
CPC ....... *G01N 21/6456* (2013.01); *A61B 5/0059* (2013.01); *A61B 2503/40* (2013.01); *G01N 21/4795* (2013.01)

(58) Field of Classification Search
CPC ............ G01N 21/4795; G01N 21/6456; A61B 5/0059; A61B 5/0064; A61B 5/0073; A61B 5/0077; A61B 5/0062; A61B 2503/40
(Continued)

(56) References Cited

U.S. PATENT DOCUMENTS 4,687,325 A 8/1987 Corby, Jr.
4,687,352 A 8/1987 Igi et al.
(Continued)

FOREIGN PATENT DOCUMENTS

EP 1 016 419 7/2000
JP 06-129984 5/1994
(Continued)

OTHER PUBLICATIONS

Schweiger M, Arridge S R, Hiraoka M and Delpy D T 1995 The finite element method for the propagation of light in scattering media: boundary and source conditions Med. Phys. 22 1779-92.*
(Continued)

*Primary Examiner* — Angela M Hoffa
*Assistant Examiner* — Helene Bor
(74) *Attorney, Agent, or Firm* — Fish & Richardson P.C.

(57) ABSTRACT

Disclosed are apparatus and methods for determining accurate optical property values of turbid media. In one embodiment, the method includes (a) providing a light source, having a first wavelength and a known illumination power, sequentially at a plurality of specific illumination positions on a first surface of the specimen; (b) for each specific position of the light source, obtaining light emission measurements from a second surface of the specimen that is opposite the first surface, wherein the light emission measurements are obtained for a plurality of surface positions of the second surface; and (c) for each specific illumination position of the light source at the first surface of the specimen, determining one or more optical properties for the specimen based on the specific illumination position of the light source, the first wavelength of the light source, the known illumination power of the light source, and the obtained light emission measurements for such each specific illumination position. The optical properties for the plurality
(Continued)

of specific illumination positions of the light source are individually determined for each specific illumination position of the light source.

17 Claims, 11 Drawing Sheets

(58) Field of Classification Search
USPC .............................. 600/473, 476; 3/473, 476
See application file for complete search history.

(56) References Cited

U.S. PATENT DOCUMENTS

| | | | |
|---|---|---|---|
| 4,761,071 A | 8/1988 | Baron | |
| 4,773,097 A | 9/1988 | Suzaki et al. | |
| 5,202,091 A | 4/1993 | Lisenbee | |
| 5,205,291 A | 4/1993 | Potter | |
| 5,242,441 A | 9/1993 | Avitall | |
| 5,319,209 A | 6/1994 | Miyakawa et al. | |
| 5,334,193 A | 8/1994 | Nardella | |
| 5,414,258 A | 5/1995 | Liang | |
| 5,452,723 A | 9/1995 | Wu et al. | |
| 5,584,872 A | 12/1996 | LaFontaine et al. | |
| 5,594,253 A | 1/1997 | Bueno et al. | |
| 5,636,299 A | 6/1997 | Bueno et al. | |
| 5,637,874 A | 6/1997 | Hammamatsu | |
| 5,650,135 A | 7/1997 | Contag et al. | |
| 5,661,562 A | 8/1997 | Aharon | |
| 5,672,881 A | 9/1997 | Striepeke et al. | |
| 5,705,807 A | 1/1998 | Throngnumchai | |
| 5,738,101 A | 4/1998 | Sappey | |
| 5,746,210 A | 5/1998 | Benaron et al. | |
| 5,807,262 A | 9/1998 | Papaioannou et al. | |
| 5,812,310 A | 9/1998 | Stewart et al. | |
| 5,813,988 A * | 9/1998 | Alfano et al. | 600/476 |
| 5,818,587 A | 10/1998 | Devaraj et al. | |
| 5,835,617 A | 11/1998 | Ohta et al. | |
| 5,840,572 A | 11/1998 | Copeland | |
| 5,865,754 A | 2/1999 | Sevick-Muraca et al. | |
| 5,867,250 A | 2/1999 | Baron | |
| 5,917,190 A | 6/1999 | Yodh et al. | |
| 5,943,129 A | 8/1999 | Hoyt et al. | |
| 5,953,446 A | 9/1999 | Opsal et al. | |
| 5,963,658 A | 10/1999 | Klibanov et al. | |
| 5,970,164 A | 10/1999 | Bamberger | |
| 5,983,121 A * | 11/1999 | Tsuchiya | 600/310 |
| 6,069,698 A | 5/2000 | Ozawa et al. | |
| 6,070,583 A | 6/2000 | Perelman et al. | |
| 6,075,610 A * | 6/2000 | Ueda et al. | 356/432 |
| 6,108,576 A | 8/2000 | Alfano et al. | |
| 6,175,407 B1 | 1/2001 | Sartor | |
| 6,205,347 B1 | 3/2001 | Morgan et al. | |
| 6,208,886 B1 | 3/2001 | Alfano et al. | |
| 6,217,847 B1 | 4/2001 | Contag et al. | |
| 6,219,566 B1 | 4/2001 | Weersink et al. | |
| 6,230,046 B1 * | 5/2001 | Crane et al. | 600/476 |
| 6,242,743 B1 | 6/2001 | DeVito et al. | |
| 6,252,623 B1 | 6/2001 | Lu et al. | |
| 6,264,610 B1 | 7/2001 | Zhu | |
| 6,267,477 B1 | 7/2001 | Karpol et al. | |
| 6,267,722 B1 | 7/2001 | Anderson et al. | |
| 6,272,367 B1 * | 8/2001 | Chance | 600/407 |
| 6,321,111 B1 | 11/2001 | Perelman et al. | |
| 6,332,087 B1 | 12/2001 | Svenson et al. | |
| 6,364,829 B1 | 4/2002 | Fulghum | |
| 6,373,557 B1 | 4/2002 | Mengel et al. | |
| 6,373,568 B1 | 4/2002 | Miller et al. | |
| 6,377,353 B1 | 4/2002 | Ellis | |
| 6,381,302 B1 | 4/2002 | Berestov | |
| 6,392,241 B1 | 5/2002 | Rushbrooke et al. | |
| 6,394,965 B1 | 5/2002 | Klein | |
| 6,403,947 B1 | 6/2002 | Hoyt et al. | |
| 6,415,051 B1 | 7/2002 | Callari et al. | |
| 6,429,943 B1 | 8/2002 | Opsal et al. | |
| 6,512,993 B2 | 1/2003 | Kacyra et al. | |
| 6,529,627 B1 | 3/2003 | Callari et al. | |
| 6,549,288 B1 | 4/2003 | Migdal et al. | |
| 6,597,931 B1 | 7/2003 | Cheng et al. | |
| 6,615,061 B1 | 9/2003 | Khalil et al. | |
| 6,615,063 B1 | 9/2003 | Ntziachristos | |
| 6,618,152 B2 | 9/2003 | Toida | |
| 6,618,463 B1 | 9/2003 | Schotland et al. | |
| 6,628,401 B2 | 9/2003 | Toida | |
| 6,628,747 B1 | 9/2003 | Schotland et al. | |
| 6,636,755 B2 | 10/2003 | Toida | |
| 6,642,953 B1 | 11/2003 | Nieto Velasco et al. | |
| 6,646,678 B1 | 11/2003 | Kobayashi | |
| 6,665,072 B2 | 12/2003 | Hoyt | |
| 6,690,466 B2 | 2/2004 | Miller et al. | |
| 6,690,520 B1 | 2/2004 | Kusuzawa | |
| 6,693,710 B1 | 2/2004 | Hoyt | |
| 6,710,770 B2 | 3/2004 | Tomasi et al. | |
| 6,748,259 B1 | 6/2004 | Benaron et al. | |
| 6,750,964 B2 | 6/2004 | Levenson et al. | |
| 6,775,349 B2 | 8/2004 | Schotland et al. | |
| 6,775,567 B2 | 8/2004 | Cable | |
| 6,813,030 B2 | 11/2004 | Tanno | |
| 6,919,919 B2 | 7/2005 | Nelson et al. | |
| 6,924,893 B2 | 8/2005 | Oldenbourg et al. | |
| 6,963,375 B1 | 11/2005 | Lundberg | |
| 7,048,716 B1 | 5/2006 | Kucharczyk et al. | |
| 7,056,728 B2 | 6/2006 | Francis et al. | |
| 7,107,116 B2 * | 9/2006 | Geng | 700/117 |
| 7,113,217 B2 | 9/2006 | Nilson et al. | |
| 7,184,047 B1 | 2/2007 | Crampton | |
| 7,263,157 B2 | 8/2007 | Bruder et al. | |
| 7,668,587 B2 | 2/2010 | Benaron et al. | |
| 2002/0001080 A1 | 1/2002 | Miller | |
| 2003/0002028 A1 | 1/2003 | Rice et al. | |
| 2003/0026762 A1 | 2/2003 | Malmros et al. | |
| 2003/0099329 A1 | 5/2003 | Schotland et al. | |
| 2004/0010192 A1 | 1/2004 | Benaron et al. | |
| 2004/0015062 A1 | 1/2004 | Ntziachristos et al. | |
| 2004/0021771 A1 | 2/2004 | Stearns et al. | |
| 2004/0027659 A1 | 2/2004 | Messerschmidt et al. | |
| 2004/0064053 A1 * | 4/2004 | Chang | A61B 5/0071 600/478 |
| 2004/0085536 A1 | 5/2004 | Schotland et al. | |
| 2004/0087862 A1 * | 5/2004 | Geng | A61B 5/0064 600/473 |
| 2004/0262520 A1 | 12/2004 | Schotland et al. | |
| 2005/0145786 A1 | 7/2005 | Rice et al. | |
| 2005/0149877 A1 | 7/2005 | Rice et al. | |
| 2005/0201614 A1 | 9/2005 | Rice et al. | |
| 2005/0237423 A1 | 10/2005 | Nilson et al. | |
| 2005/0283071 A1 | 12/2005 | Ripoll et al. | |
| 2006/0118742 A1 | 6/2006 | Levenson et al. | |
| 2006/0119865 A1 | 6/2006 | Hoyt et al. | |
| 2006/0146346 A1 | 7/2006 | Hoyt | |
| 2006/0173354 A1 * | 8/2006 | Ntziachristos | A61B 5/0073 600/476 |
| 2006/0203243 A1 | 9/2006 | Nilson et al. | |
| 2006/0203244 A1 | 9/2006 | Nilson et al. | |
| 2006/0245631 A1 | 11/2006 | Levenson | |
| 2006/0268153 A1 | 11/2006 | Rice et al. | |
| 2007/0016078 A1 | 1/2007 | Hoyt et al. | |
| 2007/0253908 A1 | 11/2007 | Rice et al. | |

FOREIGN PATENT DOCUMENTS

| | | |
|---|---|---|
| JP | 08-136448 | 5/1996 |
| JP | 09-504964 | 5/1997 |
| JP | 10-510626 | 10/1998 |
| JP | 11-173976 | 7/1999 |
| JP | 2000-500228 | 1/2000 |
| WO | 96/16596 | 6/1996 |
| WO | 97/40381 | 10/1997 |
| WO | 98/34533 | 8/1998 |
| WO | 00/17643 | 3/2000 |
| WO | 00/36106 | 6/2000 |
| WO | 00/54581 | 9/2000 |
| WO | 01/18225 | 3/2001 |
| WO | 01/63247 | 8/2001 |
| WO | 02/41760 | 5/2002 |

(56) References Cited

FOREIGN PATENT DOCUMENTS

OTHER PUBLICATIONS

International Search Report dated Feb. 11, 2008 in PCT Application No. PCT/US07/76781.
Written Opinion dated Feb. 11, 2008 in PCT Application No. PCT/US07/76781.
ASTM International, "Standard Test Method for Determining Solar or Photopic Reflectance, Transmittance, and Absorptance of Materials Using a Large Diameter Integrating Sphere," Designation E 1175-87 (Reapproved 2003), 4 pgs.
Notice of Allowance dated Sep. 16, 2009 in U.S. Appl. No. 10/606,976.
Office Action dated May 7, 2009 in U.S. Appl. No. 10/606,976.
Office Action dated Apr. 16, 2009 in U.S. Appl. No. 11/829,919.
Notice of Allowance dated Mar. 23, 2009 in U.S. Appl. No. 11/829,927.
Office Action dated Dec. 10, 2008 in U.S. Appl. No. 10/606,976.
Office Action dated Jan. 16, 2008 in Australian Patent Application No. 2003249299.
European Office Action dated Aug. 21, 2008 from EP Patent Application No. 03764754.2.
International Search Report dated Jul. 7, 2008 from PCT Application No. PCT/US08/59492.
Written Opinion dated Jul. 7, 2008 from PCT Application No. PCT/US08/59492.
Ntziachristos, Fluorescence Molecular Imaging, Annual Reviews of Biomedical Engineering, Aug. 2006, vol. 8, pp. 1-33.
Office Action dated Aug. 4, 2008 from U.S. Appl. No. 10/606,976.
Tauler et al., "Multivariate Curve Resolution Applied to Spectral Data from Multiple Runs of an Industrial Process," Analytical Chemistry, vol. 65, No. 15, Aug. 1, 1993, pp. 2040-2047.
Jaumot et al., "A graphical user-friendly interface for MCR-ALS: a new tool for multivariate curve resolution in MATLAB," Chemometrics and Intelligent Laboratory Systems 76, 2005, pp. 101-110.
Wentzell et al., "Multivariate curve resolution of time course microarray data," BMC Bioinformatics 2006, 7:343, submitted Mar. 18, 2006, published Jul. 13, 2006.
Duponchel et al., "Multivariate curve resolution methods in imaging spectroscopy: influence of extraction methods and instrumental perturbations," J. Chem. Inf. Comput. Sci., vol. 43, No. 6, 2003, pp. 2057-2067.
Notice of Allowance dated Mar. 19, 2008 from U.S. Appl. No. 10/151,463.
European Examination Report dated Apr. 8, 2008 from EP Patent Application No. 06013492.1.
Chinese Office Action dated Apr. 4, 2008 from Chinese Patent Application No. 03821121.1.
Office Action dated Jun. 9, 2008 from Japanese Patent Application No. 2002-589773.
Office Action dated Aug. 6, 2008 from U.S. Appl. No. 11/733,358.
Ghiglia et al., "Two-Dimensional Phase Unwrapping: Theory, Algorithms, and Software", Wiley-Interscience publication, 1998, ISBN 0-471-24935-1, p. 312.
Mahmood et al., "Near-Infrared Optical Imaging of Protease Activity for Tumor Detection", Radiology, Dec. 1999, p. 866-870.
Toyooka et al., "Automatic Profilometry of 3-D Diffuse Objects by Spatial Phase Detection", Applied Optics, vol. 25, No. 10, May 15, 1986, p. 1630-1633.
Tromberg et al., "Properties of Photon Density Waves in Multiple-Scattering Media", Applied Optics, vol. 32, No. 4, Feb. 1, 1993, p. 607-616.
Weissleder et al., "Shedding Light onto Live Molecular Targets", Nature Medicine, vol. 9, No. 1, Jan. 2003, p. 123-1218.
Achilefu et al., "Novel Receptor-Targeted Fluorescent Contrast Agents for In Vivo Tumor Imaging", Investigative Radiology, vol. 35(8), Aug. 200, pp. 479-485.
Arridge, "Photon-Measurement Density Functions. Part 1: Analytical Forms", Applied Optics, vol. 34, No. 31, Nov. 1, 1995, pp. 7395-7409.
Arridge, "Photon-Measurement Density Functions. Part 2: Finite-Element-Method Calculations", Applied Optics, vol. 34, No. 34, Dec. 1, 1995, pp. 8026-8037.
Australian Office Action dated Jul. 25, 2006 for Australian Application No. 2002303819.
Becker et al., "receptor-Targeted Optical Imaging of Tumors with Near-Infrared Fluorescent Ligands", Nature Biotechnology, vol. 19, Apr. 2001, pp. 327-330.
Benaron, David A., "A System for Imaging Infection and Gene Expression in the Body in 3-D," Biomedical Optical Spectroscopy and Diagnostics, 1998 Technical Digest, 1998, Optical Society of America, pp. 134-135.
Bevilacqua et al., "In Vivo Local Determination of Tissue Optical Properties: Applications to Human Brain", Applied Optics, vol. 38, No. 22, Aug. 1, 1999, pp. 4939-4950.
Bevilacqua et al., "Monte Carlo Study of Diffuse Reflectance at Source-Detector Separations Close to One Transport Mean Free Path", Optical Society of America, vol. 16, No. 12, Dec. 1999, pp. 2935-2945.
Bouvet et al., "Real-Time Optical Imaging of Primary Tumor Growth and Multiple Metastatic Events in a Pancreatic Cancer Orthotopic Model", Cancer Research, vol. 62, Mar. 1, 2002, pp. 1534-1540.
Chang et al., "Improved Reconstruction Algorithm for Luminescence Optical Tomography When Background Lumiphore is Present", Applied Optics, vol. 37, No. 16, Jun. 1, 1998, pp. 3547-3552.
Cheong et al., "A review of the Optical Properties of Biological Tissues", IEEE Journal of Quantum Electronics, vol. 26, No. 12, Dec. 1990, pp. 2166-2185.
Contag et al., "Photonic Detection of Bacterial Pathogens in Living Hosts", Molecular Microbiology, vol. 18, No. 4, 1995, pp. 593-603.
Contag et al., "Use of Reporter Genes for Optical Measurements of Neoplastic Disease In Vivo", Neoplasia, vol. 2, Nos. 1-2, Jan.-Apr. 2000, pp. 41-52.
EP Search Report dated Oct. 6, 2006 for EP Application No. EP 06 01 3492.
Eppstein et al., "Biomedical Optical Tomography Using Dynamic Parameterization and Bayesian Conditioning on Photon Migration Measurements", Applied Optics, vol. 38, No. 10, Apr. 1, 1999, pp. 2138-2150.
Francis et al, "Visualizing Pneumococcal Infections in the Lungs of Live Mice Using Bioluminescent *Streptococcus pneumoniae* Transformed with a Novel Gram-Positive lux Transponson", Infection and Immunity, vol. 69, No. 5, pp. 3350-3358.
Frohn, "Super-Resolution Fluorescence Microscopy by Structured Light Illumination," Dissertation submitted to the Swiss Federal Institute of Technology, Zurich, 2000.
Haskell et al., "Boundary Condition for the Diffusion Equation in Radiative Transfer", Optical Society of America, vol. 11, No. 10, Oct. 1994, pp. 2727-2741.
Hastings, "Chemistries and Colors of Bioluminescent Reactions: a Review", Gene, vol. 173, 1996, pp. 5-11.
Hawrysz et al., "Developments Toward Diagnostic Breast Cancer Imaging Using Near-Infrared Optical Measurements and Fluorescent Contrast Agents", Neoplasia, vol. 2, No. 5 Sep.-Oct. 2000, pp. 388-417.
Ishimaru, "Wave Propagation and Scattering in Random Media", vol. 1, Single Scattering and Transport Theory, Academic Press, 1978.
Ishimaru, "Wave Propagation and Scattering in Random Media", vol. 2, Multiple Scattering Turbulence Rough Surfaces and Remote Sensing, Academic Press, 1978.
Kienle, "Noninvasive Determination of the Optical Properties of Two-Layered Turbid Media", Applied Optics, vol. 37, No. 4, Feb. 1, 1998, pp. 779-791.
Maston (editor), "Biological Techniques: Fluorescent and Luminescent Probes for Biological Activity: A Practical Guide to Technology for Quantitative Real-Time Analysis", Second Edition, Academic Press, 1999.
Ntziachristos et al., "Experimental Three-Dimensional Fluorescence Reconstruction of Diffuse Media by Use of a Normalized Born Approximation", Optical Society of America, vol. 26, No. 12, Jun. 15, 2001, pp. 893-895.

(56) References Cited

OTHER PUBLICATIONS

Ntziachristos et al., "Fluorescence Molecular Tomography Resolves Protease Activity In Vivo", Nature Medicine, vol. 8, No. 7, Jul. 2002, pp. 757-760.

Office Action received in EP Application No. 03764754.2 dated Feb. 7, 2007.

Pickering et al., "Double-integrating-sphere system for measuring the optical properties of tissue," Applied Optics, Feb. 1, 1993, vol. 32, No. 4, pp. 399-410.

Prahl et al., "Determining the Optical Properties of Turbid Media by Using the Adding-Doubling Method", Applied Optics, vol. 32, No. 4, Feb. 1, 1993, pp. 559-568.

Rehemtulla et al., "Rapid and Quantitative Assessment of Cancer Treatment Response Using In Vivo Bioluminescence Imaging", Neoplasia, vol. 2, No. 6, 2000, pp. 491-495.

Research & Development (magazine), vol. 42, No. 9, Sep. 2000, Part 1 of 2.

Rice et al., "Advances in 2D In Vivo Optical Imaging Instrumentation," Abstract No. 186, Society for Molecular Imaging $2^{nd}$ Annual Meeting, Aug. 2003.

Rice et al., "In Vivo Imaging of Light-Emitting Probes", Journal of Biomedical Optics, vol. 6, No. 4, Oct. 2001, pp. 432-440.

Takeda et al., "Fourier-Transform Method of Fringe-Pattern Analysis for Computer-Based Topography and Interferometry", Optical Society of America, vol. 72, No. 1, Jan. 1982, pp. 156-160.

Tuchin, "Tissue Optics: Light Scattering Methods and Instruments for Medical Diagnosis", SPIE Press, 2000.

Weissleder et al., "In Vivo Imaging of Tumors with Protease-Activated Near-Infrared Fluorescent Probes", Nature Biotechnology, vol. 17, Apr. 1999, pp. 375-378.

Windsor et al., "Imaging Pulmonary Inflammation Using Fluorescence Molecular Tomography," Society for Molecular Imaging, Sep. 23, 2005.

Wu et al., "Noninvasive Optical Imaging of Firefly Luciferase Reporter Gene Expression in Skeletal Muscles of Living Mice", Molecular Therapy, vol. 4, No. 4, Oct. 2001, pp. 297-306.

Yang et al., "Whole-Body Optical Imaging of Green Fluorescent Protein-Expressing Tumors and Metastases", PNAS, vol. 97, No. 3, Feb. 1, 2000, pp. 1206-1211.

Zhang et al., "Rapid In Vivo Functional Analysis of Transgenes in Mice Using Whole Body Imaging of Luciferase Expression," Transgenic Research, vol. 10, 2001, pp. 423-434.

Mouaddib et al., "Recent Progress in Structured Light in Order to Solve the Correspondence Problem in Stereo Vision", International Conference of Robotics and Automation, Albuquerque, New Mexico, Apr. 1997 pp. 130-136.

Battle et al., "Recent Progress in Coded Structured Light as a Technique to Solve the Correspondence Problem: A Survey", Pattern Recognition, vol. 31, No. 7, 1998, pp. 963-982.

Fofi et al., "Uncalibrated Vision Based on Structured Light", Proceedings of the 2001 IEEE International Conference on Robotics and Automation, Seoul, Korea, May 2001, pp. 3548-3553.

Scharstein et al., "High-Accuracy Stereo Depth Maps Using Structured Light", IEEE Computer Society Conference on Computer Vision and Pattern Recognition (CVPR) 2003), vol. 1, Madison, Wisconsin, pp. 195-202.

Notice of Allowance dated Aug. 24, 2009 in U.S. Appl. No. 11/829,919.

Office Action dated Nov. 17, 2009 in U.S. Appl. No. 11/127,346.

Summons to attend oral proceedings dated Sep. 28, 2009 for European Application No. 03764754.2.

Office Action dated Jul. 13, 2010 in U.S. Appl. No. 12/569,842.

Notice of Allowance dated Jul. 13, 2010 in U.S. Appl. No. 11/127,346.

Notice of Allowance dated Nov. 3, 2010 from U.S. Appl. No. 12/569,842.

Office Action dated Dec. 28, 2010 from U.S. Appl. No. 12/823,019.

Office Action dated May 24, 2011 from U.S. Appl. No. 12/823,019.

European Office Action for European Patent Application No. EP 08 745 172.0 dated Apr. 19, 2017.

\* cited by examiner

APPARATUS AND METHODS FOR DETERMINING OPTICAL TISSUE PROPERTIES

CROSS-REFERENCE TO RELATED APPLICATIONS

This application claims priority under 35 U.S.C. § 119(e) and is a non-provisional of U.S. Provisional Application No. 60/840,247, filed on Aug. 24, 2006 and titled "Fluorescent Imaging," by Rice et al., which application is herein incorporated by reference in its entirety for all purposes.

BACKGROUND OF THE INVENTION

The present invention relates to imaging technology. In particular, it relates to systems and methods that facilitate the measuring and/or imaging of a fluorescent or bioluminescent light source or light source distribution inside a scattering medium, which is particularly useful in biomedical imaging and research applications.

Imaging with light is steadily gaining popularity in biomedical applications. One currently popular light imaging application involves the capture of low intensity light emitted from a biological sample such as a mouse or other small animal. This technology is known as in vivo optical imaging. Light emitting probes that are placed inside the sample typically indicate where an activity of interest might be taking place. In one application, cancerous tumor cells are labeled with light emitting reporters or probes, such as bioluminescent proteins, or fluorescent proteins or dyes.

Photons emitted by labeled cells scatter in the tissue of the mammal, resulting in diffusive photon propagation through the tissue. As the photons diffuse, many are absorbed, but a fraction reaches the surface of the mammal. The photons emitted from surface of the mammal can then be detected by a camera. Light imaging systems capture images that record the two-dimensional (2D) spatial distribution of the photons emitted from the surface.

Using this 2D imaging data and computer-implemented photon diffusion models, a 3D representation of the fluorescent light sources inside a sample can be produced. For instance, a fluorescent probe's 3D location, size, and brightness can be determined using diffusion models. However, since these models are a function of the optical property values for the sample, the accuracy of the 3D light source representation produced by a given model depends on the accuracy of the optical properties that are input into such model.

Improved techniques and apparatus for providing accurate optical properties of a sample or a set of samples are needed.

SUMMARY OF THE INVENTION

Accordingly, apparatus and methods for determining accurate optical property values are disclosed. In one embodiment, a method of determining optical properties in a specimen is disclosed. The method includes (a) providing a light source, having a first wavelength and a known illumination power, sequentially at a plurality of specific illumination positions on a first surface of the specimen; (b) for each specific position of the light source, obtaining light emission measurements from a second surface of the specimen that is opposite the first surface, wherein the light emission measurements are obtained for a plurality of surface positions of the second surface; and (c) for each specific illumination position of the light source at the first surface of the specimen, determining one or more optical properties for the specimen based on the specific illumination position of the light source, the first wavelength of the light source, the known illumination strength of the light source, and the obtained light emission measurements for such each specific illumination position. The optical properties for the plurality of specific illumination positions of the light source are individually determined for each specific illumination position of the light source.

In further aspects, operations (a) through (c) are repeated for a second wavelength of the light source that differs from the first wavelength. In a specific implementation, the determined optical properties for each specific illumination position comprise reduced scattering $\mu_s'$ and absorption $\mu_A$. In a further aspect, the optical properties for each specific illumination position are determined by continuing to vary values for $\mu_s'$ and $\lambda_A$ in a forward model, that simulates light emitted at the second surface of the specimen in response to a light source having the first wavelength and the known illumination strength and positioned at the specific illumination position, until the output of such forward model is within a predetermined specification of the light emission measurements for such specific illumination position. In a further aspect, the forward model treats the input light as a point source located a distance $1.2/\mu_s'$ from the first surface, along with three additional image sources. In another aspect, a surface topography of the subject second surface is measured and utilized in the forward model of photon propagation. In yet another aspect, emitted light from the second surface is modeled using a diffusion model with a planar boundary tangent to a local surface element.

In another embodiment, the light source is calibrated so as to measure the power of the light source. In another aspect, the determined optical properties are used to correct optical properties derived from a Monte Carlo or Finite Element Model (FEM) simulation of heterogeneous tissue properties so that the simulation can be used to determine an internal light source distribution for the specimen, wherein the uncorrected simulation was set up for a different specimen.

In an alternative embodiment, the invention pertains to an imaging apparatus for determining optical properties of a specimen. The apparatus includes one or more light sources that are positionable at a plurality of illumination positions relative to a first surface of the specimen and a detector positioned to detect light emission measurements from a second surface of the specimen that is opposite of the first surface. The apparatus also includes at least a processor and at least a memory. The at least one processor and/or at least one memory are configured to perform one or more of the above described method operations. In another embodiment, the invention pertains to at least one computer readable storage medium having computer program instructions stored thereon that are arranged to perform one or more of the above described operations.

These and other features of the present invention will be presented in more detail in the following specification of the invention and the accompanying figures, which illustrate by way of example the principles of the invention.

DETAILED DESCRIPTION OF THE SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general, there are several applications within the field of in-vivo light imaging in which it would be desirable to provide accurate optical property values, such as reduced scattering, $\mu_S'$, and absorption, $\mu_A$, for a particular specimen or set of specimens. One application is in-vivo light imaging of a specimen in which one or more fluorescent or bioluminescent probes have been internally placed.

Figure 1:
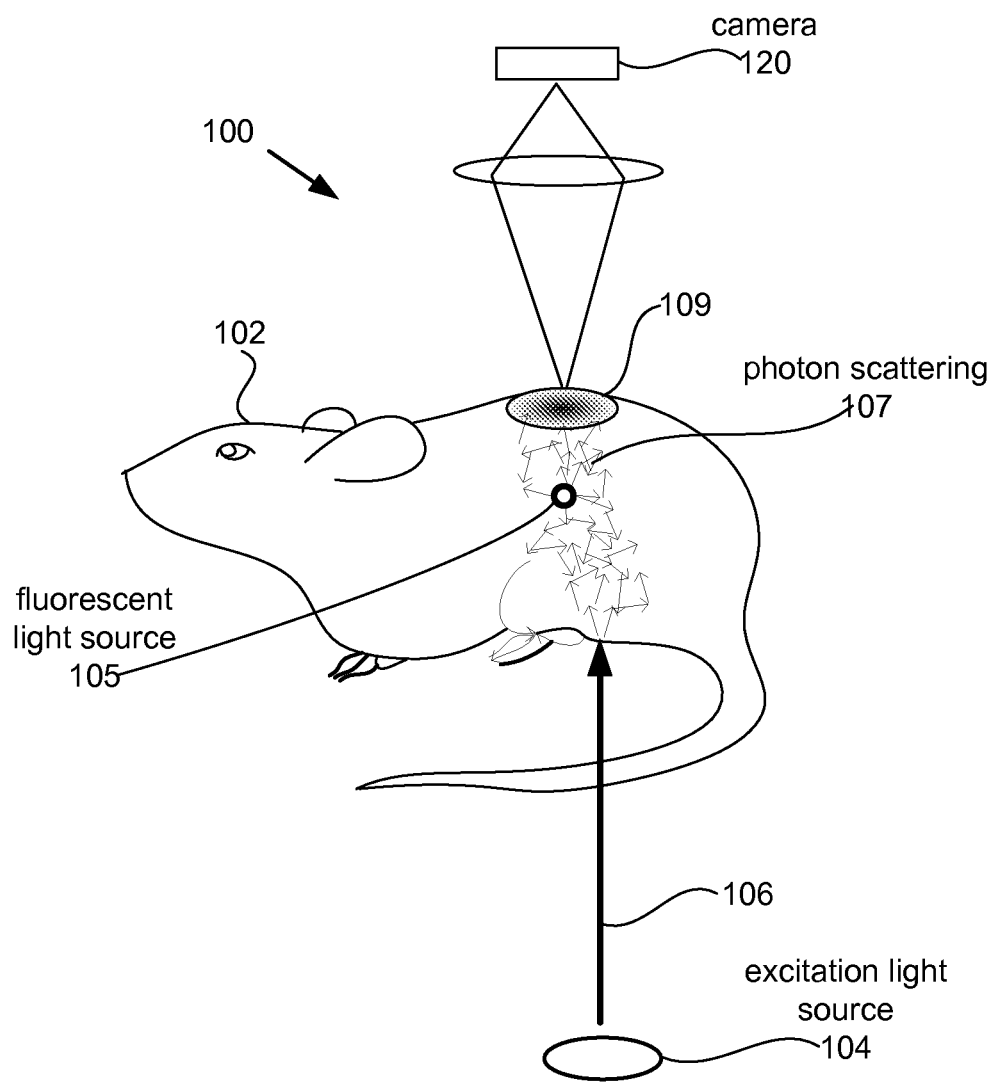
FIG. 1 shows a simplified pictorial of diffusive light propagation into, through, and out from, a mouse.

FIG. 1 shows an exemplary and simplified illustration of in-vivo light imaging, using an internal fluorescent probe. An excitation light source 104 produces incident light 106 that enters a portion of mouse 102. The incident light 106 scatters in the mouse tissues and some of it eventually reaches an internal fluorescent probe 105. When excited by incident light 106, fluorescent probe 105 emits fluorescent light 107 from within mouse 102. The fluorescent photons 107 scatter and travel through tissue in the mouse to one or more surfaces 109; the light emitted from the surface may then be detected by a camera 120.

Thus, as light 106 and 107 diffuses through the mouse, some of the light is absorbed, but a fraction of the light propagates to a surface that faces the camera 120. For fluorescent imaging, there is a two-stage diffusion: a) incident light 106 from an incident surface to fluorescent probe 105, and b) emitted fluorescent light 107 from fluorescent probe 105 to the one or more surfaces 109.

Fluorescent probe 105 generally refers to any object or molecule that produces fluorescent light. The fluorescent probe 105 absorbs incident energy of a certain wavelength or wavelength range and, in response, emits light energy at a different wavelength or wavelength range. The absorption of light is often referred to as the "excitation", while the emission of longer wave lights as the "emission". The output wavelength range is referred to herein as 'output spectrum'. Fluorescent probe 105 may include one or more fluorescent light emitting molecules, called 'fluorophores'. A fluorophore refers to a molecule or a functional group in a molecule that absorbs energy of a specific wavelength and re-emits energy at a different wavelength. Many commercially available fluorophores are suitable for use with mouse 2. Suitable fluorophores include Qdot® 605, Qdot® 800, AlexaFluor® 680 and AlexaFluor® 750 as provided by Invitrogen of San Diego, Calif. Both organic and inorganic substances can exhibit fluorescent properties, and are suitable for use with fluorescent probe 105. In one embodiment, fluorescent probe 105 emits light in the range of about 400 nanometers to about 1300 nanometers.

The fluorescent probe distribution may be internal to any of a variety of light-emitting objects, animals or samples that contain light-emitting molecules. Objects may include, for example, tissue culture plates and multi-well plates (including 96, 384 and 864 well plates). Animals including a fluorescent probe distribution may include mammals such as a human, a small mammal such as a mouse, cat, primate, dog, rat or other rodent. Other animals may include birds, zebra-fish, mosquitoes and fruit flies, for example. Other objects and samples are also suitable for use herein, such as eggs and plants. For ease of discussion, the remaining disclosure will show and describe a mouse 102 as an imaging object that contains a fluorescent probe.

Techniques can be utilized to model the light propagation in mouse 102 to determine 3D parameters of fluorescent probe 105 and solve for the internal fluorescent probe distribution 105, given images from the mouse 102 that are captured by the camera and a set of optical properties for the mouse 102.

In one technique, a trans-illumination process is utilized to determine the 3D parameters of fluorescent probe S. In a trans-illumination imaging system, an excitation light source illuminates a fluorescence source in an object from a side opposite to a receiving camera. A trans-illumination system typically works to separate the excitation light from the emission light. For example, the excitation light may come from below a sample for an overhead camera that captures the emission light. Suitable examples of such a trans-illumination assembly are described in (1) U.S. Pat. No. 7,177,024, entitled "BOTTOM FLUORESCENCE ILLUMINATION ASSEMBLY FOR AN IMAGING APPARATUS", issued 13 Feb. 2007 by David Nilson et al. and (2) U.S. patent application Ser. No. 11/434,605, entitled "AN ILLUMINATION SYSTEM FOR AN IMAGING APPARATUS WITH LOW PROFILE OUTPUT DEVICE", filed 15 May 2006 by David Nilson et al. This patent and application are incorporated by reference in their entirety for all purposes. An example trans-illumination imaging system is also further described below.

Often, by illuminating the specimen through a bottom side illumination thereof with an excitation light source, as opposed to a topside illumination of the specimen, the autofluorescence background signal of the specimen itself is reduced. This reduction of autofluorescence is due to a higher number of tissue autofluorescence photons being emitted on the side of the excitation light source than on the side facing the camera. In the case of a topside illumination, both the camera and the excitation light source are on the same side.

Figure 2:
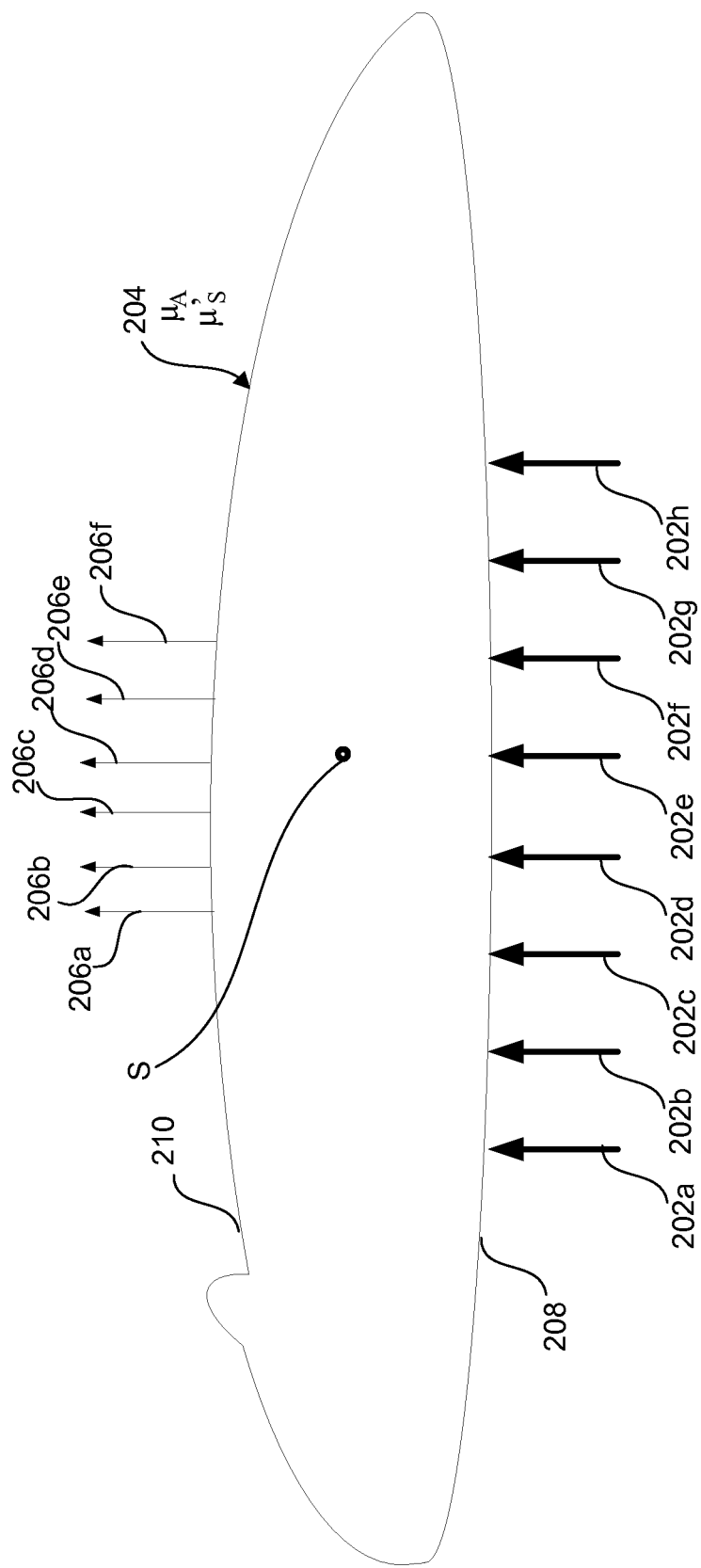
FIG. 2 is a diagrammatic representation of a mouse which is assumed to be homogenous with optical properties $\mu_S'$ and $\mu_A$ for the purposes of determining the 3D parameters of fluorescent probe S.

FIG. 2 is a diagrammatic representation of a mouse 204 which is assumed to be homogenous with optical properties reduced scattering $\mu_S'$ and absorption $\mu_A$ for the purposes of determining the 3D parameters of fluorescent probe S. In this illustration, trans-illumination is utilized. As shown, one or more light sources sequentially emit light at positions 202a through 202h on an illumination surface 208 of mouse 204. For each illumination position, light emission can be detected at a plurality of positions 206a through 206f, for example, on an emission surface 210 of the mouse 204 that is opposite the illumination surface 208. The light emission from surface 210 is generally emitted by fluorescent probe S in response to illumination being applied to a particular illumination position, e.g., 202d, on illumination surface 208.

In a specific embodiment, a Green's function is used to model internal light propagation from an internal light source, such as probe S, to surface elements of the opposite surface 210. A Green's function mathematically describes light propagation through space, such as through tissue, from one location to another. In one embodiment, the Green's function uses volume elements and surface mesh elements of the specimen as vector spaces for its data elements that depend on the optical properties of the mouse 204. For instance, the mouse 204 is conceptually divided into a plurality of volume elements that each have the same values for $\mu_S'$ and $\mu_A$. Once the Green's function is determined, the distribution of an internal source, such as probe S, is obtained by solving the system of linear equations that relate the photon density at the surface to the source distribution inside the specimen.

Techniques for providing the transport properties $\mu_S'$ and $\mu_A$ that are then used to determine internal light distribution have several disadvantages under some conditions. For instance, the transport properties may be determined under rigorous measurements conditions for a homogeneous slab using a light source that is not calibrated. The uncalibrated light source may result in inaccurate determinations of the transport properties. The homogeneous slab, for which the transport properties are determined, may also differ significantly from the specimen for which internal light distribution is being determined based on the determined transport properties.

Additionally, although $\mu_S'$ and $\mu_A$ can be assumed to be uniform across the volume elements of the mouse 204 and can be used to adequately determine internal light distribution, actual $\mu_S'$ and $\mu_A$ values are not uniform across a live specimen. That is, different tissue types of the specimen have different $\mu_S'$ and $\mu_A$ values and, accordingly result in different light propagation results through such different tissues. If different light propagation models were utilized for different areas of the specimen to account for non-uniform $\mu_S'$ and $\mu_A$ values (or non-uniform values), this treatment would likely result in a more accurate determination of internal light distribution in a specimen, as compared to assuming uniform $\mu_S'$ and $\mu_A$ values for such specimen. Accordingly, specific embodiments of the present invention provide more accurate values for $\mu_S'$ and $\mu_A$, for example, to facilitate determination of the source distribution inside the specimen. These transport parameters $\mu_S'$ and $\mu_A$ may also be determined utilizing the surface topography of the specimen, as opposed to a rectangular slab, as described further below.

Figure 3:
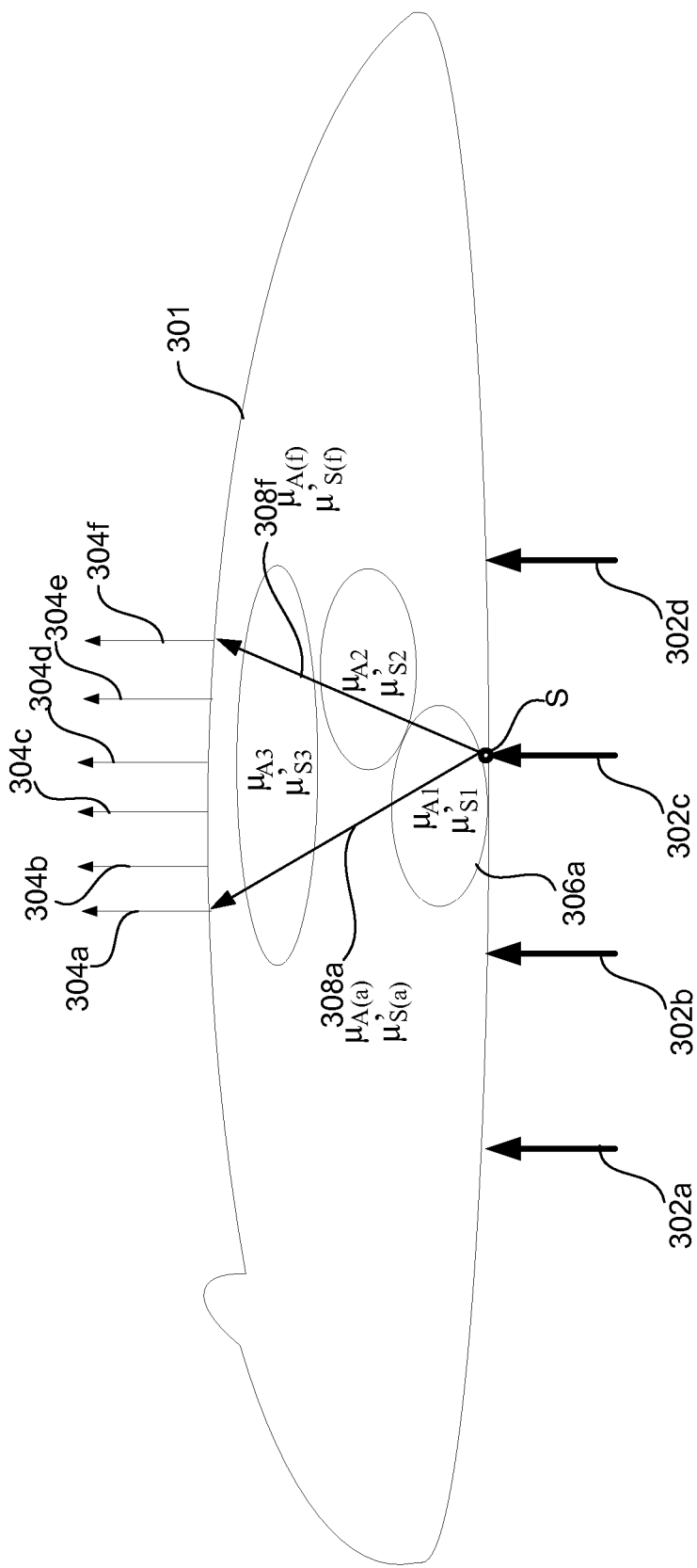
FIG. 3 is a diagrammatic representation of a mouse which is assumed to be heterogeneous or homogeneous for the purposes of determining optical property values, e.g., $\mu_S'$ and $\lambda_A$, in accordance with one embodiment of the present invention.

FIG. 3 is a diagrammatic representation of a mouse which is assumed to be heterogeneous or homogeneous for the purposes of determining optical property values, e.g., $\mu_S'$ and $\mu_A$, in accordance with one embodiment of the present invention. In this case, the optical properties of the specimen 301 are unknown while a known light source S is utilized for determining the unknown optical properties. That is, an unknown or uncalibrated internal light source, such as a fluorescent probe, is not used.

Utilization of a trans-illumination arrangement allows potentially non-uniform optical properties to be determined for different positions of an illumination source. As shown, light source S illuminates the specimen at a selected position 302c on a bottom surface of the specimen. The light source S has a known position with respect to the specimen, a known illumination strength, and a known wavelength.

Light is emitted from the specimen 301 at a plurality of emission positions 304 in response to known light source S at position 302c. Light propagation between the light source S and each emission position 304 can be conceptually described as light propagation along vectors 308 from the light source S to each emission position 304. Although the light propagation between each pair of light source S and emission position is shown as a vector, the light propagation is actually diffuse. Each vector 308 can be conceptualized as passing through different volumes of the specimen having different actual transport characteristics. For instance, vector 308a passes through a volume having transport values $\mu_{S1}'$ and $\mu_{A1}$ and $\mu_{S3}'$ and $\mu_{A3}$ to result in light emission at position 304a. Another vector 308f passes through three volumes having the following transport values: (i) $\mu_{S1}'$ and $\mu_{A1}$, (ii), $\mu_{S2}'$ and $\mu_{A2}$, and (iii) $\mu_{S3}'$ and $\mu_{A3}$, respectively, to result in light emission at position 304f. Although each vector may pass through tissues having different optical properties, each vector can be described as having a single set of optical properties (e.g., an average set of $\mu_S'$ and $\mu_A$).

For a light source at a particular position, the optical properties may be assumed to be homogenous. For example, a single set of optical properties are determined for each of the vectors 308. Alternatively, different sets of optical properties may be determined for each vector. As shown, optical properties $\mu_{S(a)}'$ and $\mu_{A(a)}$ are determined for vector 308a. Optical properties $\mu_{S(a)}'$ and $\mu_{A(a)}$ are determined for vector 308f. The optical properties for vector 308a may be determined to differ or be the same as the optical properties for vector 308f. In either case, optical properties can be determined for several different illumination positions, e.g., positions 302a through 302d.

Figure 4A:
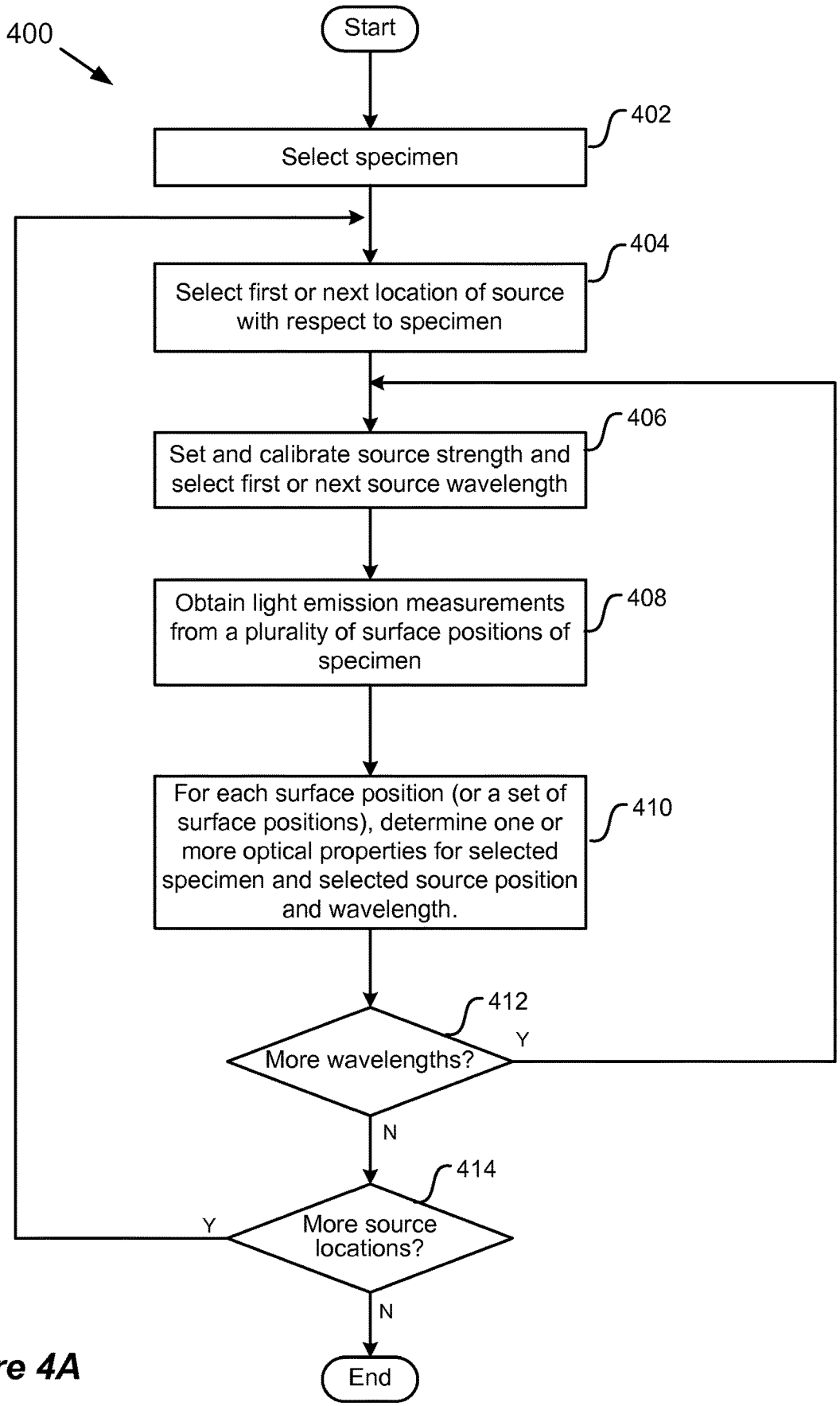
FIG. 4A is a flow chart illustrating a procedure for determining optical properties in accordance with one implementation of the present invention.

FIG. 4A is a flow chart illustrating a procedure 400 for determining optical properties in accordance with one implementation of the present invention. As shown, a specimen is initially selected in operation 402. The specimen may take any suitable form, such as a homogeneous slab, a phantom specimen which mimics the shape and optical properties of a real animal such as a mouse, or a live specimen such as a live mouse.

Figure 5:
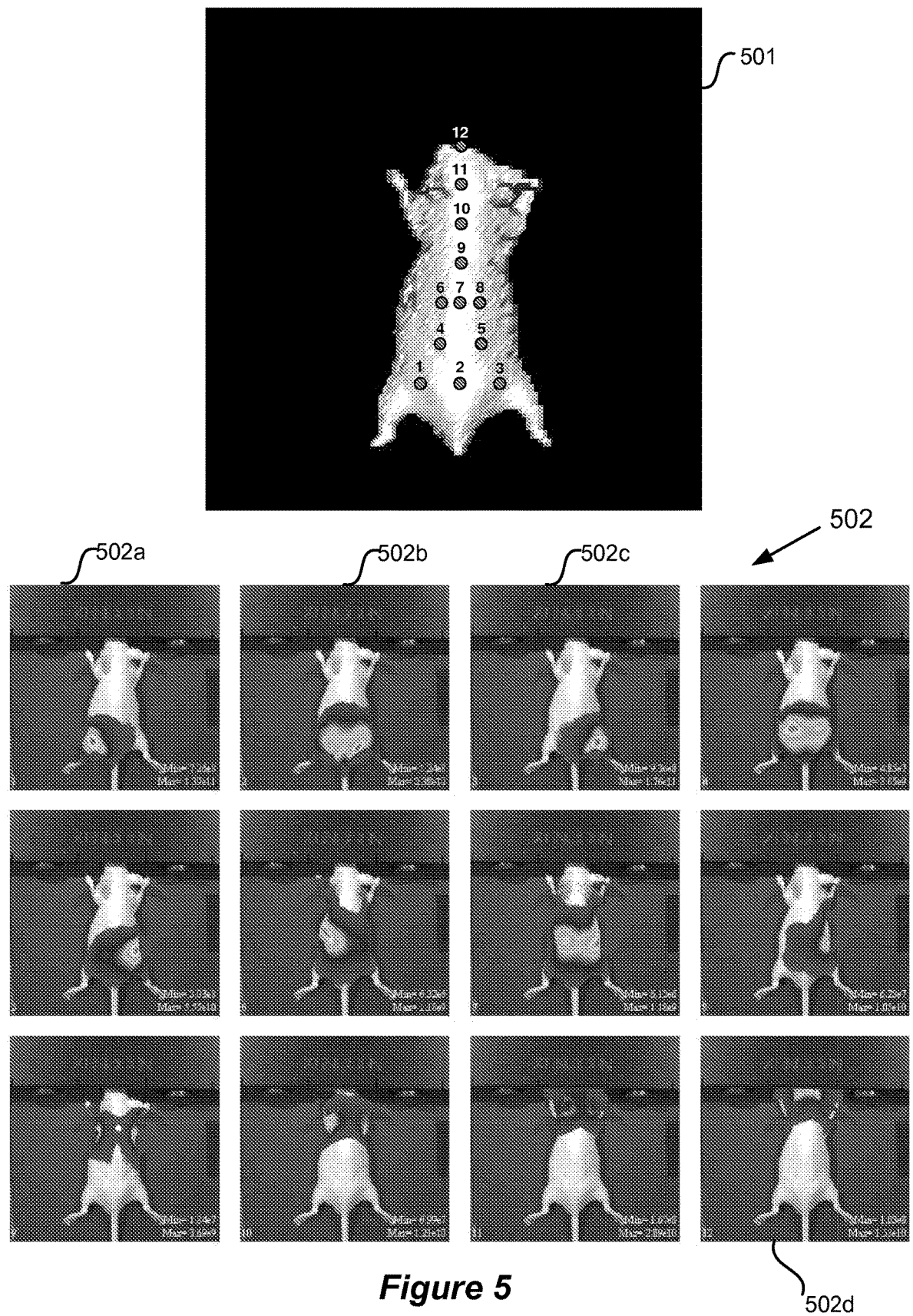
FIG. 5 includes a plurality of emission images obtained for a plurality of trans-illumination positions in accordance with one embodiment of the present invention.

A first location of the light source with respect to the specimen may then be selected in operation 404. FIG. 5 illustrates a specimen image 501 of a mouse having 12 specific illumination positions 1 through 12 that are distributed across a surface of the specimen. For instance, the specimen is positioned directly on a glass plate and a light source is focused on about a 2 mm diameter spot at a specific one of positions 1 through 12 on a top surface of the glass plate. A non-reflective sheet having holes at each illumination position may also be placed between the source and the specimen to reduce the amount of stray light escaping around the specimen.

The light source's strength may then be set and calibrated and a first source wavelength is selected in operation 406. For example, the light source's injected power is measured using a spectral power meter to determine the known illumination strength. Also, the source may be a broadband illumination source that is filtered to define the incident wavelength (e.g., 30 nm bandwidth).

Light emission measurements for a plurality of surface positions may then be obtained in operation 408. The light emission measurements are obtained from a surface that is opposite of the illumination surface. In one implementation, a point source is focused on a bottom surface of the specimen, while radiance is measured at multiple positions of the top surface of the specimen. The radiance at the top surface (or other emission surface) of the specimen may be imaged with a CCD (charge coupled detector) camera. The imaging path may be configured with a narrow band emission filter (20 nm bandwidth) to match the wavelength of the excitation filter and block other unwanted wavelengths.

When a complex surface, such as a mouse, is used, techniques of the present invention may also include mapping the measured 2D fluorescent image data onto the complex surface of the mouse or the like. A surface representation of at least a portion of the mouse is initially obtained. The surface portion may include all of the mouse, or a smaller portion. In this case, the methods also employ topographic determination tools. Topographic imaging determines a surface representation of an object, or a portion thereof. In one embodiment, the present invention uses structured light to determine a surface topography for at least a portion of the mouse. Tomographic imaging refers to information inside the mouse surface. An exemplary illustration of topographic vs. tomographic imaging uses a 2D planar slice through the mouse: topography gives the surface (the outer bounding line), while tomography provides information inside the bounding surface.

The surface representation refers to a mathematical description or approximation of the actual surface of the mouse, or a portion thereof. The surface representation need not include the entire mouse, and may include a portion of the mouse relevant to a particular imaging scenario. Suitable techniques to obtain a surface representation include structured light, or another imaging modality such as computer tomography (CT) or magnetic resonance imaging (MRI), for example. The surface representation may be divided into a surface mesh comprising a set of surface elements.

In one embodiment, structured light is used to obtain a surface representation of the mouse. Structured light uses a set of lines of light that are projected down on the mouse at an angle (at about 30 degrees, for example) to the surface normal. The mouse generates structured light surface information as each light line reacts to the shape of the animal. Cumulatively, the lines of light each bend or alter in spacing as they pass over the mouse. The structured light surface information can be measured by a camera and used to determine the height of the surface at surface portions of the mouse that are illuminated by the structured light source. These surface portions are the portions of the mouse that face the camera (for a current position of the mouse relative to the camera). The position of the mouse relative to the camera may be changed to gain multiple structured light images and structured light information from multiple views.

A camera captures the structured light surface information, digitizes the information and produces one or more structured light images. A processor, operating from stored instructions, produces a 3D surface representation of the mouse (or a portion of the object facing the camera) using the structured light information. More specifically, a processing system, running on stored instructions for generating a topographic representation (a surface map) from the structured light surface information, builds a 3D topographic representation of the mouse using the structured light surface information. If multiple views are used, structured light topographies from these multiple views may be "stitched together" to provide a fuller surface representation from different angles. Structured light image capture, hardware and processing suitable for use with a mouse or the like is described further in co-pending U.S. patent application Ser. No. 11/127,842, entitled "STRUCTURED LIGHT IMAGING APPARATUS", filed 11 May 2005 by David Nilson et al., which is incorporated herein by reference in its entirety. Several embodiments of tomographic modeling are further described in co-pending U.S. patent application Ser. No. 11/733,358, entitled "FLUORESCENT LIGHT TOMOGRAPHY", filed 10 Apr. 2007 by Bradley W. Rice et al., which is incorporated by reference in its entirety for all purposes.

Once the surface topography is determined, the measured image data in the 2D images can be mapped to image data at a surface of the mouse or the like. This process converts 2D light data collected at a camera to 3D light data at a 3D surface of the mouse. In one embodiment, the mapping converts radiance data from the measured images to photon density just inside the surface. The mapping manipulates 2D camera data according to the geometry between the mouse surface and the camera lens to derive values of the light emission intensity (or radiance) at the surface.

Emission of light from a mouse surface may be specified in units of radiance, such as photons/sec/cm$^2$/steradian. In one embodiment, an imaging system captures images of the mouse and reports surface intensity in units of radiance. Surface radiance can be converted to photon density just inside the mouse surface, using a model for photon propagation at the tissue-air interface, as described herein. When the surface representation includes a set of surface elements, the mapping may produce a surface emission data vector that includes photon density at each surface element for the mouse topography. The photon density just inside the surface is then related to a light source that diffuses inside the mouse tissue according to a diffusion model.

Tomographic techniques use the light emission data from the mouse surface, along with tomographic imaging software that models light propagation internal to the mouse, and solves for optical properties of the mouse or the like. The modeling includes both a) excitation light propagation from the excitation light source, and its entry points into the mouse, and b) light propagation from inside the mouse to the surfaces captured in the images.

Figure 4B:
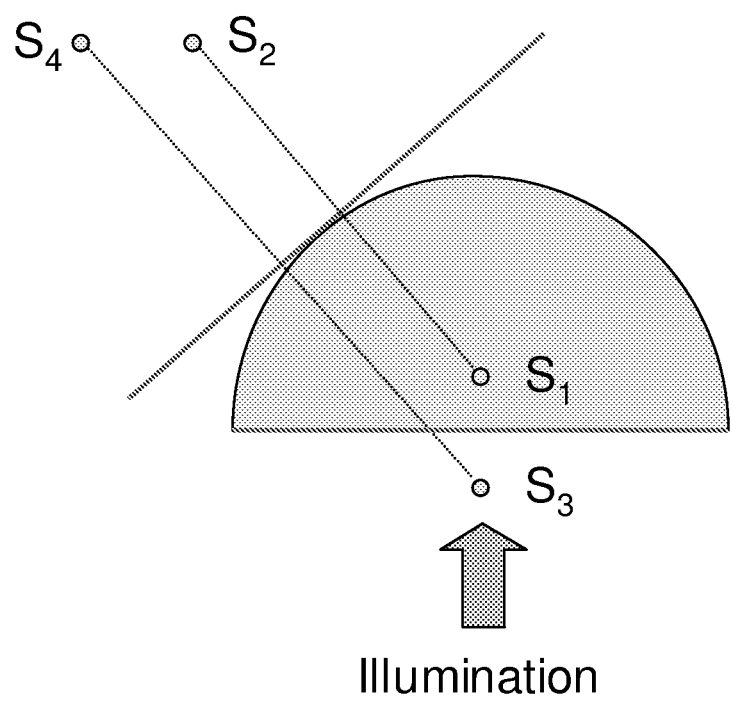
FIG. 4B shows a point source fitting algorithm used in a forward model that determines, given an excitation source, what is obtained on the surface.

FIG. 4B shows a point source fitting algorithm used in a forward model that determines, given an excitation source, what is obtained on the surface. As illustrated, the fitting function may operate to simulate the radiance on the dorsal surface, assuming the effective source ($S_1$) is a distance $1.2/\mu_S$ inside the bottom surface. In one embodiment, the forward model assumes a homogeneous medium, tangent plane approximation with hybrid boundary conditions (e.g., an extrapolated and partial current boundary). For instance, the emitted light from the second surface may be modeled using a diffusion model with a planar boundary tangent to the local surface element. The model may utilize one fixed image source ($S_3$) at the bottom surface and two image sources ($S_2$, $S_4$) at the top surface that move with the tangent plane.

FIG. 5 includes a plurality of emission images 502 obtained for a plurality of trans-illumination positions 1 through 12 on specimen 501 in accordance with one embodiment of the present invention. By way of examples, emission image 502a results from illumination at position 1; emission image 502b results from illumination at position 2; emission image 502c results from illumination at position 3; and emission image 502d results from illumination at position 12.

For each surface (or for a set of surface positions), one or more optical properties are then determined for the selected specimen and the selected source position and wavelength in operation 410. It may then be determined whether there are any other wavelengths to be assessed in operation 412. That is, optical properties are preferably determined for multiple wavelengths and for each illumination position. When there are more wavelengths, a next source wavelength is selected in operation 406 and the emission measurements are obtained and analyzed for a plurality of emission positions in operations 408 and 410. In other words, optical properties are determined for a next source wavelength and the same first illumination position.

When optical properties are determined for all desired wavelengths for a particular source position, it may also be determined whether there are other source locations to select in operation 414. The procedure for determining optical properties may be repeated for any number of illumination positions and wavelengths.

The optical properties may be determined in any suitable manner. For instance, a forward model for a homogeneous medium with a complex surface may be utilized to simulate surface emission and determine unknown optical properties for a known point source. Further description of a suitable forward model is described in the above referenced U.S. patent application Ser. No. 11/733,358 entitled "FLUORESCENT LIGHT TOMOGRAPHY", which application is incorporated herein by reference in its entirety for all purposes. In general, the radiance that is determined by a forward model can then be compared to the measured radiance. When the simulated radiance is within a predetermined specification of the measured radiance, the optical properties are determined for the fitted results. Fitting to the radiance might provide a unique determination of the transmissivities of absorption and scattering, $\mu_A$ and $\mu'_S$ respectively, in living mice, for a portion of the mouse or the entire mouse. The portion may refer to a specific anatomical structure (e.g., kidney, lung, etc.) or material type (e.g., bone, flesh, etc.)

In one implementation, a weighting function can be applied in a $\chi^2$ evaluation to get a fit for the measured data:

$$\chi^2 = \sum_i (y_i - L_i)^2 w_i$$

where, $L_i$ is the measured radiance for each position of the surface, $y_i$ is the simulated radiance for each position of the surface, and $w_i$ is the weighting function for each position of the surface.

The weighting function acts as a spatial filter. It can be set to zero if the pixel is within a threshold distance of the edge of the mouse mesh (e.g., 0.25 cm). It can also be set to zero if the pixel radiance is less than a threshold level (e.g., 1% of the peak radiance). Otherwise the $w_i$ can be set to provide statistical weighting, such as by setting to $1/L_i$.

The forward model is used to simulate emission at the surface for a given set of optical properties. One function for simulating light propagation through multiple volume elements (e.g., from element i to element j) can be determined based on a linear relationship between the source strength in each volume element and the photon density at each surface element that is described by a Green's function $G_{ij}$, the photon density at the jth surface element may be approximated by the sum of the contributions from all the volume elements:

$$\rho_j \cong \sum_i G_{ij} S_i$$

where $$G_{ij} = \frac{1}{2\pi D} \left\{ \frac{\exp(-\mu_{eff} r_{ij})}{r_{ij}} - \frac{1}{z_b} \exp(r_{ij}/z_b) E_1 \left[ \left( \mu_{eff} + \frac{1}{z_b} \right) r_{ij} \right] \right\}$$

Here $r_{ij}=|x_j-x_i|$, $E_1$ is the first order exponential integral and $$\mu_{eff} = \sqrt{3\mu_A(\mu_A + \mu'_S)}$$

$$z_b = \frac{2D}{c} \frac{1 + R_{eff}}{1 - R_{eff}}$$

Here $R_{eff}$ is the effective internal reflectivity of the surface averaged over all incident angles, $D=1/3(\mu_A+\mu_S')$, and c is speed of light. The radiance may be normalized to unit area in the image plane. Then applying the partial current boundary condition, the following equation can be obtained:

$$L = \frac{1}{4\pi n^2} T(\theta_1) \left[ 1 + \frac{3}{2} \frac{1 - R_{eff}}{1 + R_{eff}} \cos\theta_1 \right] \rho$$

Here T is the transmission through the surface from inside the slab and $\theta_1$ is the internal angle of incidence onto the surface.

Figure 6A:
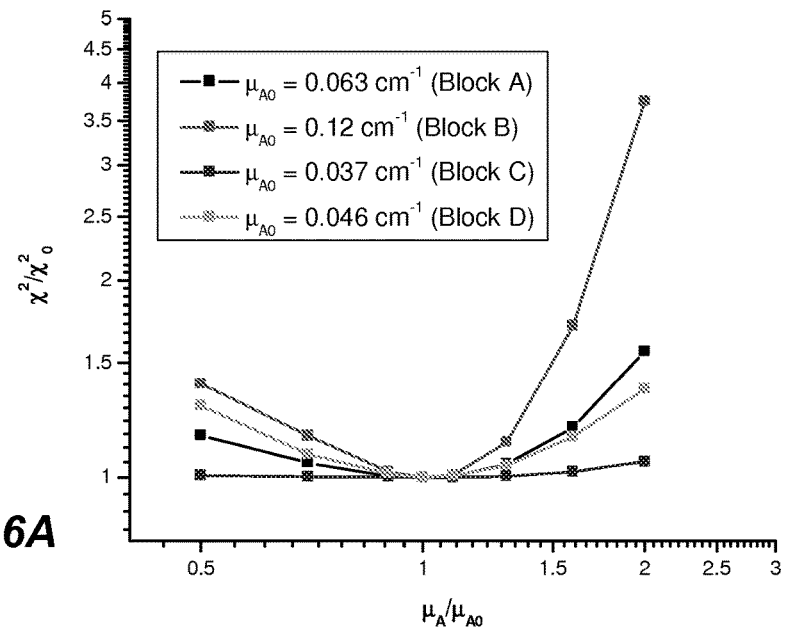
FIGS. 6A through 6C are graphs of $\chi^2$ as a function of $\mu_A$, $\mu_S'$, and the index of refraction, respectively, in accordance with results produced from techniques of the present invention.
Figure 6B:
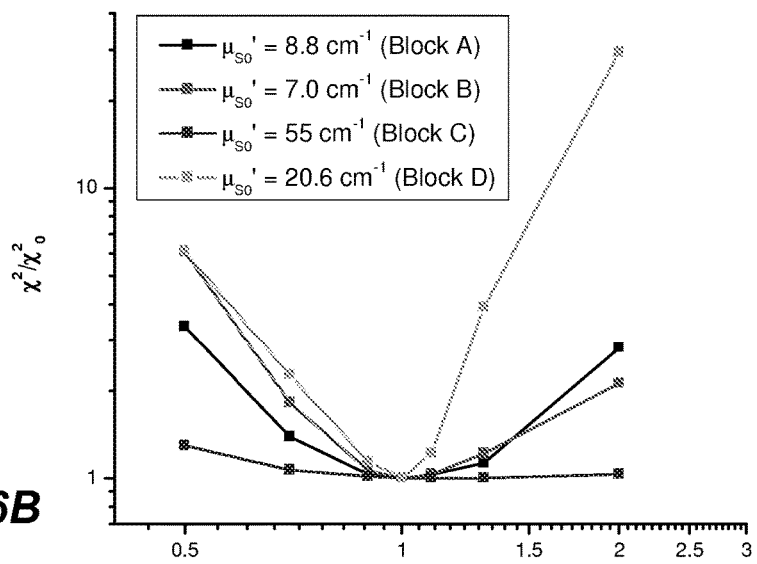
Figure 6C:
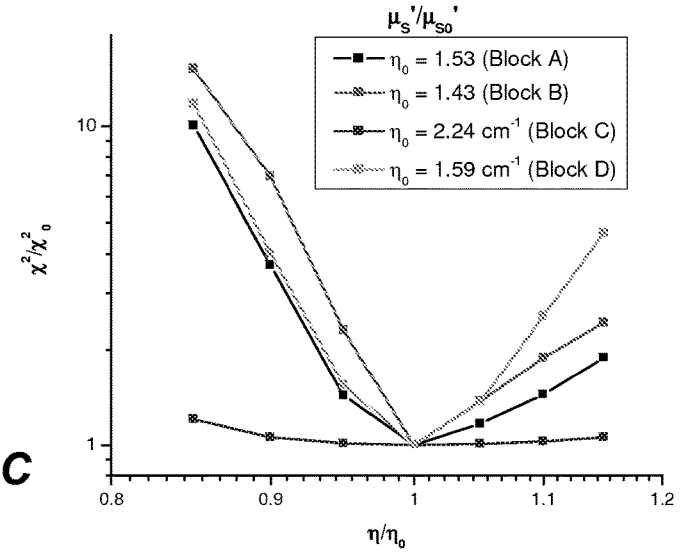

A unique set of optical properties can be determined for a calibrated illumination position by adjusting the value of one fitting parameter about its optimum value and measuring the change in $\chi^2$ for the fit while the other parameters were free to vary. A deep minimum in $\chi^2$ tends to indicate a unique, independent evaluation of the parameter. FIGS. 6A through 6C show the dependence of $\chi^2$ on the values of the parameters $\mu_A$, $\mu_S'$ and $\eta$, respectively, for different homogeneous slabs. It can be seen that slabs A, B and D have fairly sharp minima for all of the parameters, indicating that the solution is unique for these cases. In contrast, the minima are very shallow for slab C, so that there is significant uncertainty in the fitting procedure. The reason for this behavior for slab C may be related to the fact that this slab has the largest ratio of $\mu_S'/\mu_A$, and hence the diffusion coefficient D has virtually no dependence on $\mu_A$. These techniques for determining a unique set of optical properties are contemplated as being applied to a live specimen, such as a live mouse.

Figure 7A:
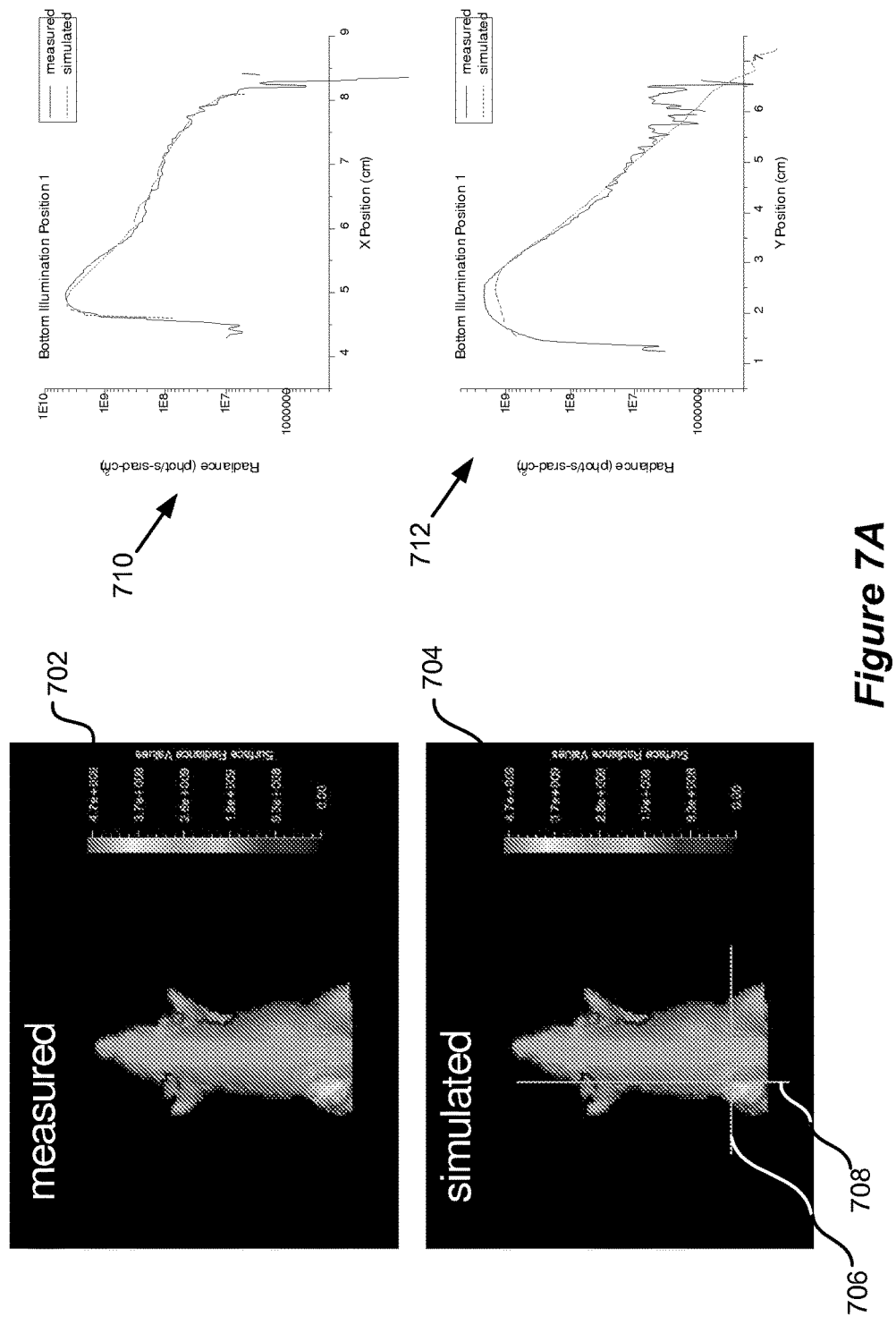
FIG. 7A shows a comparison between measured trans-illumination radiance values and simulated radiance values for a set of $\mu_S'$ and $\mu_A$ values that were determined with the techniques of the present invention.

Sample results for a phantom mouse are shown in FIG. 7. The phantom mouse was imaged using a 640 nm source having a known source strength and located at a specific position (i.e., position 1 of FIG. 5). A measured image 702 and a simulated image 704 were obtained for such source settings. A forward model was then used to determine optical properties that resulted in a minimum $\chi^2$ value. The resulting measured values and simulated values along an x axis and a y axis are shown in graphs 710 and 712, respectively. That is, graph 710 shows the simulated and measured radiance for x axis 706 and graph 712 shows the simulated and measured radiance for y axis 708 after $\chi^2$ has been minimized. As shown, the measured and simulated radiance are plotted in log units and show substantial matching between the simulated and measured values.

Figure 7B:
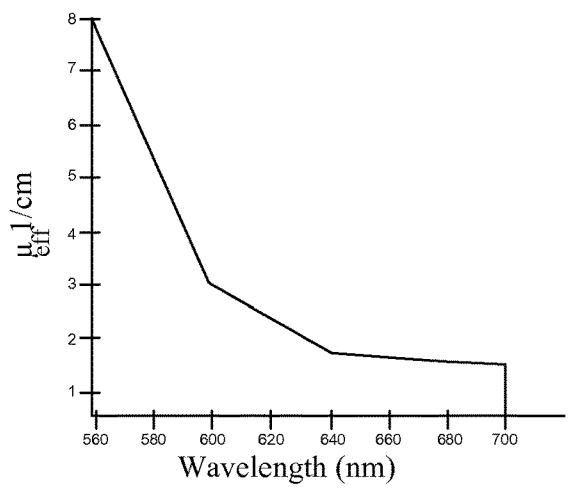
FIG. 7B is a graph of example results for $\mu_{eff}$ as a function of wavelength, as determined with techniques of the present invention.

From these fits to the forward model, the parameters $\mu_A$, $\mu_S'$, and hence $\mu_{eff}$, can be determined as a function of wavelength as shown in FIG. 7B.

In sum, trans-illumination mode allows for controlled (i.e. known wavelength and intensity) light injection with precise, programmable positioning that facilitates quantitative determination of optical transport. One area of interest is trans-illumination of phantom slabs. The trans-illumination configuration is potentially advantageous for determining unambiguously the transport parameters of homogeneous slab samples. Another important application is the trans-illumination of a phantom specimen, such as a phantom mouse. Trans-illumination measurements can also provide a rigorous test of a 3D model for photon transport in homogeneous media and complex geometries. Finally, trans-illumination measurements may be applied to determine photon transport properties of a living mouse. One goal of may be to assess the importance of heterogeneities in modulating the photon transport in a living mouse.

A quasi-homogeneous model has been found to be a reasonable approach to simulating transillumination in living mice. This result may be because a lot of averaging takes place as light diffuses through the entire thickness of the mouse. Unfortunately the quasi-homogeneous model may not be valid for the cases of more practical interest in which the light source, fluorescent or bioluminescent, is imbedded inside the mouse. In these cases the transport parameters may be very much dependent on the exact position of the source, and a spatially detailed anatomical model can then be preferably used. In a specific implementation, a more exact treatment of the optical properties of a mouse with heterogeneous tissue properties may be achieved by utilizing a three dimensional Monte Carlo or Finite Element Model (FEM) computational model. In these types of simulations, the optical properties are assumed to vary in each volume element. Light propagation through a particular specimen can be simulated using finite elements with specific properties for the heterogeneous tissues of such specimen. Such simulations are typically performed for a particular specimen where a full 3D model of the anatomy exists, and the results would be less accurate for a different specimen. In the present invention, a new specimen may be measured using trans-illumination so as to determine average optical properties along each propagation vector. These average optical property values can then be used to correct or adjust the optical properties obtained from Monte Carlo or FEM simulations so that the simulation can be accurately be applied to the new specimen. For instance, the corrected simulations may then be utilized to accurately determine internal light distribution for the new specimen, taking into account the heterogeneous nature of such specimen.

A transport parameter look-up table (TPLUT) or the like may be provided, and this TPLUT may be based on a particular specimen, such as the female mouse atlas. The TPLUT defines effective values of D and $\mu_{eff}$ for each voxel-surface element pair that is derived from a series of finite element simulations of photon diffusion using the complete anatomical model. The transport parameters $\mu_A$ and $\mu_S'$ for this female mouse atlas are listed in Tables I and II, respectively. The 'background' category refers to the tissue surrounding the organs, bones and blood vessels. The background is expected to be some combination of fat and muscle; however, the background can also be assigned the values measured for muscle. Using these transport parameters, a female mouse TPLUT may be built for each of the wavelengths of 600, 640, 680 and 700 nm

TABLE I

Values of the absorption coefficient $\mu_A$ in units of 1/cm assigned to the female mouse atlas:

| Tissue Type | 560 nm | 600 nm | 640 nm | 680 nm | 700 nm |
|---|---|---|---|---|---|
| Background | 5.07 | 1.87 | 0.88 | 0.67 | 0.58 |
| Bladder | 5.50 | 1.21 | 0.35 | 0.24 | 0.23 |
| Blood | 19.37 | 5.98 | 1.82 | 1.02 | 0.66 |
| Bone | 11.38 | 6.37 | 1.94 | 1.38 | 1.07 |
| Brain | 10.36 | 2.87 | 0.69 | 0.55 | 0.43 |
| Colon | 8.30 | 3.08 | 1.15 | 0.77 | 0.61 |
| Heart | 31.37 | 13.23 | 4.73 | 3.55 | 2.79 |
| Kidney | 19.24 | 5.06 | 1.65 | 1.12 | 0.85 |
| Liver | 19.37 | 5.98 | 1.82 | 1.02 | 0.66 |
| Lung | 36.66 | 9.65 | 3.18 | 2.44 | 1.98 |
| Muscle | 5.07 | 1.87 | 0.88 | 0.67 | 0.58 |
| Pancreas | 6.74 | 2.18 | 0.92 | 0.64 | 0.47 |
| Spleen | 48.86 | 10.53 | 2.28 | 1.23 | 0.72 |
| Stomach | 8.60 | 3.59 | 1.71 | 1.05 | 0.84 |

TABLE II

Values of the scattering coefficient $\mu_S'$ in units of 1/cm assigned to the female mouse atlas:

| Tissue Type | 560 nm | 600 nm | 640 nm | 680 nm | 700 nm |
|---|---|---|---|---|---|
| Background | 9.84 | 9.29 | 9.13 | 8.87 | 8.85 |
| Bladder | 5.66 | 4.48 | 4.66 | 4.65 | 4.80 |
| Blood | 8.91 | 8.42 | 7.97 | 7.58 | 7.40 |
| Bone | 15.27 | 16.31 | 14.81 | 12.77 | 12.54 |
| Brain | 17.39 | 16.79 | 16.22 | 15.65 | 15.40 |
| Colon | 10.77 | 11.36 | 11.17 | 10.62 | 10.46 |
| Heart | 16.12 | 15.37 | 14.7 | 14.11 | 13.85 |
| Kidney | 12.66 | 11.90 | 11.21 | 10.61 | 10.33 |
| Liver | 8.91 | 8.42 | 7.97 | 7.58 | 7.40 |
| Lung | 45.30 | 44.38 | 43.52 | 42.74 | 42.37 |
| Muscle | 9.84 | 9.29 | 9.13 | 8.87 | 8.85 |
| Pancreas | 15.92 | 15.72 | 15.11 | 14.63 | 14.19 |
| Spleen | 8.25 | 7.85 | 7.49 | 7.17 | 7.02 |
| Stomach | 11.69 | 11.63 | 11.62 | 11.23 | 11.03 |

The transillumination measurements can be used to evaluate the error and thereby calibrate the TPLUT. This is because the transillumination radiance images directly correspond to a subset of the information contained in the TPLUT: the photon transport between a voxel at the ventral surface and the surface elements on the dorsal surface. One approach is to assume that the error is entirely in the $\mu_{eff}$ values (not the D values). When the radiance, measured at the $i^{th}$ surface element due to transillumination at a particular source position, is considered, the photon density $\rho_i$ at that surface element can found by inverting the above equation for L. Now $\rho_i$ can be compared to the value $\rho_o$ of the photon density predicted by the TPLUT.

In general, the TPLUT is simply a look-up table of transport parameters. The photon density can be calculated by applying a forward model as described herein, but using the transport parameters given by the TPLUT for each voxel-surface element pair. However, the TPLUT is defined in the coordinate system of the specific female mouse atlas. In order to model the data obtained on a living mouse, a volume transformation may be applied to the TPLUT that maps the voxels and surface elements of the atlas mouse to those of the living mouse (the 'target'). This volume transformation can be created by co-registering the atlas and target mouse surfaces. Once the volume transformation has been applied to the TPLUT, the transillumination of the living mouse can be modeled with a full heterogeneous treatment.

It can be assumed that the $i^{th}$ surface element the TPLUT value of $\mu_{\mathit{eff}}^o$ for the absorption yields a photon density of $\rho_o$. A revised value of absorption, $\mu_{\mathit{eff}}^i$ can be determined so that the photon density is brought into agreement with the value $\rho_i$ given by the transillumination measurement. The relationship between the photon density and $\mu_{\mathit{eff}}$ in an infinite medium can be written as, $$\rho = \frac{1}{4\pi Dr}\exp(-\mu_{\mathit{eff}} r)$$

where r is the distance between the source and the surface element. Here the variation of ln $\rho$ with $\mu_{\mathit{eff}}$ is exactly linear. The forward model then can include the effects of the boundary. However, it is expected that the dependence of ln $\rho$ on $\mu_{\mathit{eff}}$ will still be essentially linear and well approximated by the first order Taylor series term:

$$\ln\rho_i - \ln\rho_o = \frac{\partial \ln\rho}{\partial \mu_{\mathit{eff}}}(\mu_{\mathit{eff}}^i - \mu_{\mathit{eff}}^o)$$

Hence we can write an expression for the correction factor $C_i$ defined as:

$$C_i \equiv \frac{\mu_{\mathit{eff}}^i - \mu_{\mathit{eff}}^o}{\mu_{\mathit{eff}}^o} = \left(\frac{\partial \ln\rho}{\partial \mu_{\mathit{eff}}}\mu_{\mathit{eff}}^o\right)^{-1}(\ln\rho_i - \ln\rho_o)$$

The quantity $\partial \ln \rho/\partial\mu_{\mathit{eff}}$ can be determined numerically for each surface element by making two forward calculations of $\rho_i$ using slightly different values of $\mu_{\mathit{eff}}$:

$$\frac{\partial \ln\rho}{\partial \mu_{\mathit{eff}}} = \frac{\ln\rho_i(\mu_{\mathit{eff}}^o + \Delta\mu) - \ln\rho_i(\mu_{\mathit{eff}}^o - \Delta\mu)}{2\Delta\mu}$$

where $\Delta\mu=0.01\mu_{\mathit{eff}}^o$. The correction factors $C_i$ can be calculated for all of the surface elements that are within a radius of 0.75 cm from the source position in the image plane. Then these values can be averaged to determine the mean correction factor for the source position. In this way, mean correction factors for each of the 12 different source positions, for example, can be determined. The next step can include transforming the source positions back into the coordinate system of the female mouse atlas, using the inverse volume transformation. It can be assumed that the values at positions 1 and 3 represent the error in the values of the 'background' since these are located in the thigh region which are mostly muscle and fat. The average value of these two correction factors can then be determined and assigned to the perimeter of the mouse. Then, a process may be implemented so as to interpolate over the image plane to produce a correction factor mapping over the entire surface of the mouse atlas.

Correction maps for each individual mouse type may then be obtained. The correction factors have been found to vary slightly from mouse to mouse, which is consistent with the scatter of the quasi-homogenous transport parameter results. The correction maps serve as a valuable guide for calibrating the TPLUT. The transport parameters for the various organs in the atlas model can be revised according to, $$\mu_A' = (1-C)^2 \mu_A^o$$

$$\mu_S' = \mu_S'^o - C(2+C)\mu_A^o$$

Here the correction factors C can be inferred from the global correction maps at each wavelength. The TPLUT can then be rebuilt using the full heterogeneous model of the mouse anatomy with these revised transport parameters. This new TPLUT can be calibrated against the transillumination measurements.

Figure 8:
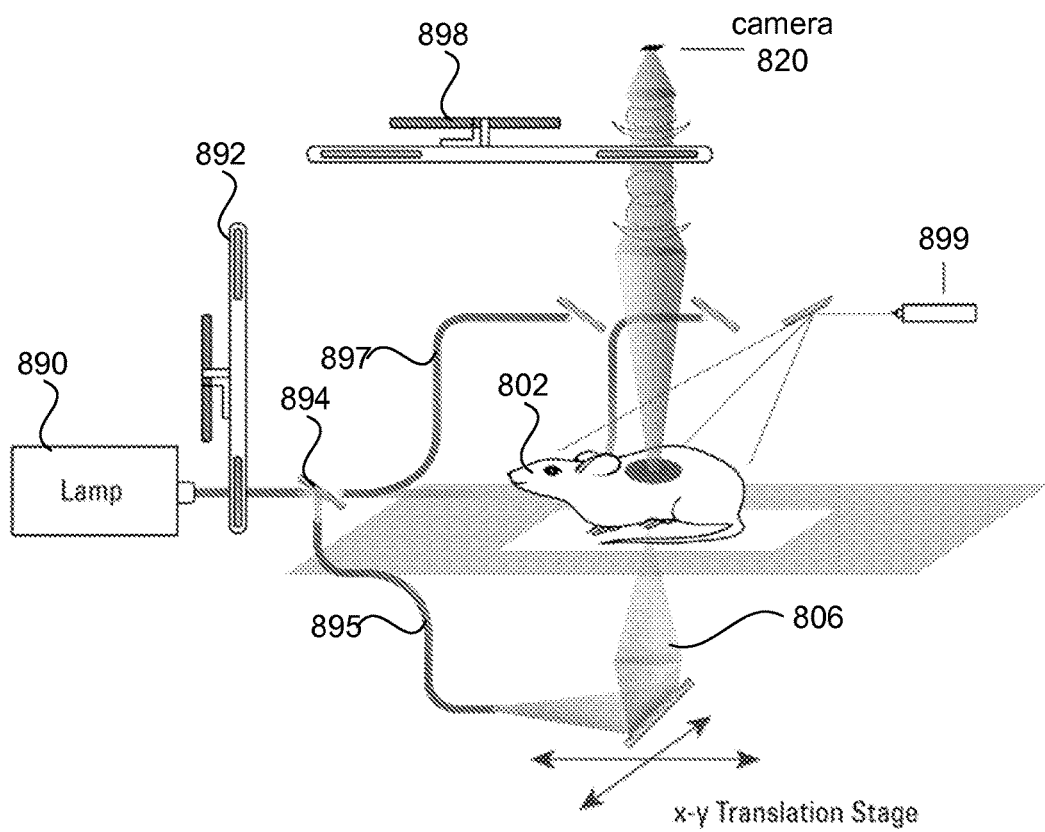
FIG. 8 schematically shows a trans-illumination system in accordance with one embodiment.

Any suitable imaging system may be utilized to determine optical properties for a known light source and then use such determined optical properties in accordance with various techniques of the present invention. FIG. 8 schematically shows a trans-illumination system in accordance with one embodiment. Trans-illumination provides light from a side of the mouse opposite to the camera (e.g., incident light from below and a camera above), so that the light travels through the mouse. This provides lower levels of autofluorescence, which is useful for 3D tomographic reconstructions. Also, the ability to move the trans-illumination point relative to a fluorescent probe fixed within the animal, provide additional information that is used for optical property determination and/or 3D tomographic reconstructions.

In the trans-illumination mode, the excitation light source 804 includes a lamp 890 that provides light that passes through a filter in excitation filter wheel 892, which allows a user to change the spectrum of the incident excitation light. A fiber bundle switch 894 directs the excitation light into one of two paths 895 and 897. Path 895 is used for trans-illumination and directs the incident light along a fiber bundle or cable for provision towards a bottom surface of the mouse 802. In one embodiment, the outlet position of path 895 can be moved or re-directed with respect to the specimen to create multiple incident excitation light locations of trans-illumination path 895.

Epi-illumination provides the incident light from the same side of the animal that an image is captured (e.g., incident light from above, and a camera above the mouse), and is often referred to as reflection-based fluorescent imaging. In this mode, switch 894 directs the excitation light into path 897, where it routs to a position above the mouse for provision towards a top surface of the mouse 802 on the same side of the mouse as camera 820.

Epi-illumination provides a faster survey of the entire animal, but may be subject to higher levels of autofluorescence. Both trans-illumination and epi-illumination may be used for analysis of the specimen. Epi-illumination avoids significant light attenuation through the mouse, and may help constrain volume elements near the camera-facing surface of the mouse. For example, the epi-illumination constraints may identify artifact voxels near the top surface, which are then removed by software.

In either case, an emission filter 898 allows a user to control a spectrum of light received by camera 820. This combination of excitation filter wheel 892 and emission filter 898 allows images to be captured with numerous combinations of excitation and emission wavelengths. In a specific embodiment, excitation filter wheel 892 includes twelve filters while emission filter 898 includes 24 positions.

Imaging may also capture both trans- and epi-illumination images, and combine the data. In each view, the light takes a different path through mouse, which provides a different set of input criteria and internal light conditions for tomographic reconstruction calculations.

A structured light source 899 also provides structured light onto the top of the animal for structured light image capture by the camera 820 without moving the mouse 802 on the horizontal surface.

In another embodiment, the stage is moveable, which allows camera 820 to capture images from multiple perspectives relative to the mouse 802. The stage may move in one dimension (e.g., up and down or side to side) or two dimensions for example.

In one embodiment, the fluorescent excitation uses a different spectrum than the fluorescent emission. As one of skill in the art will appreciate, the bandgap between excitation and emission filters will vary with the imaging system used to capture the images. A bandgap of at least 25 nm is suitable for many imaging systems. The excitation spectrum may be achieved using any combination of lights and/or filters. The emission spectrum will depend on a number of factors such as the fluorophore used, tissue properties, whether an emission filter is used before the camera, etc. In one embodiment, the trans-illumination location of the excitation light source is moved to capture multiple images of internal fluorescence and the same set of excitation and emission filters is used for the different excitation light source positions.

A camera then captures a fluorescent light image of at least a portion of the mouse. The fluorescent image records fluorescence as a function of 2D position. The image may include the entire mouse, or a portion of interest that has been zoomed in on (optically or digitally). The image is transferred to the image processing unit and/or computer for subsequent processing.

In another embodiment, multiple images are taken for differing trans-illumination positions of the excitation light source 806. Each trans-illumination position provides a different set of input conditions for determination of a specimen's optical properties and/or for providing tomographic reconstruction. In this case, the imaging system is configured to move the excitation light source (or has multiple excitation light sources that are controllably turned on/off) and captures an image of the mouse for each different trans-illumination position of the excitation light source.

All of the images may be used to determine optical properties of the specimen and/or to perform a tomographic reconstruction, or a subset can be used. The subset may be selected based on a quality measure for the images, such as a threshold for number of fluorescent photons collected in each image. Other quality measures may be used to select the images. The number of images captured may vary. In one embodiment, 1 to about 80 different trans-illumination positions and images are suitable for tomographic reconstruction. In a specific embodiment, from about 4 to about 50 images are suitable. The images may be stored for optical property determination and/or tomographic assessment at a later time, e.g., the images—or a subset thereof—are recalled from memory during optical property determination and/or tomographic processing.

In one embodiment, the stage and mouse may then be moved to a second position. While the stage is at the second position, one or more photographic, structured light, and/or fluorescent images of the mouse may be captured. Image collection may further continue by capturing images of the sample from additional positions and views. For example, image capture may occur at anywhere from 2 to 200 positions of the mouse within an imaging chamber. In general, as more images are captured, more information is gathered for tomographic reconstruction. Also, multiple structured light positions may be used to images more of the mouse in 3D. Eight positions, spaced every 45 degrees about a nose-to-tail axis of the mouse, is suitable in some 3D embodiments to build a stitched together surface representation for 360 degree viewing about the mouse.

In one embodiment, image capture is automated. A user may initiate software included with an imaging system that controls components of the imaging system responsible for image capture. For example, the user may launch imaging and acquisition software on a computer associated with the imaging system that initializes the camera and carries out imaging automatically. According to stored instructions, the software may then select a desired stage position if a moveable stage is used, prepare the system for photographic, structured light, and/or fluorescent image capture (e.g., turn on/off lights in the box), focus a lens, selectively position an appropriate excitation or emission filter, select an excitation fluorescent light source (one of many for example), set an f-stop, transfer and store the image data, build a reconstruction, etc. For fluorescent image capture, software activates the camera to detect photons emitted from the mouse, which usually corresponds to absolute units from the surface. The camera may capture the fluorescent image quickly or over an extended period of time (up to several minutes).

Figure 9A:
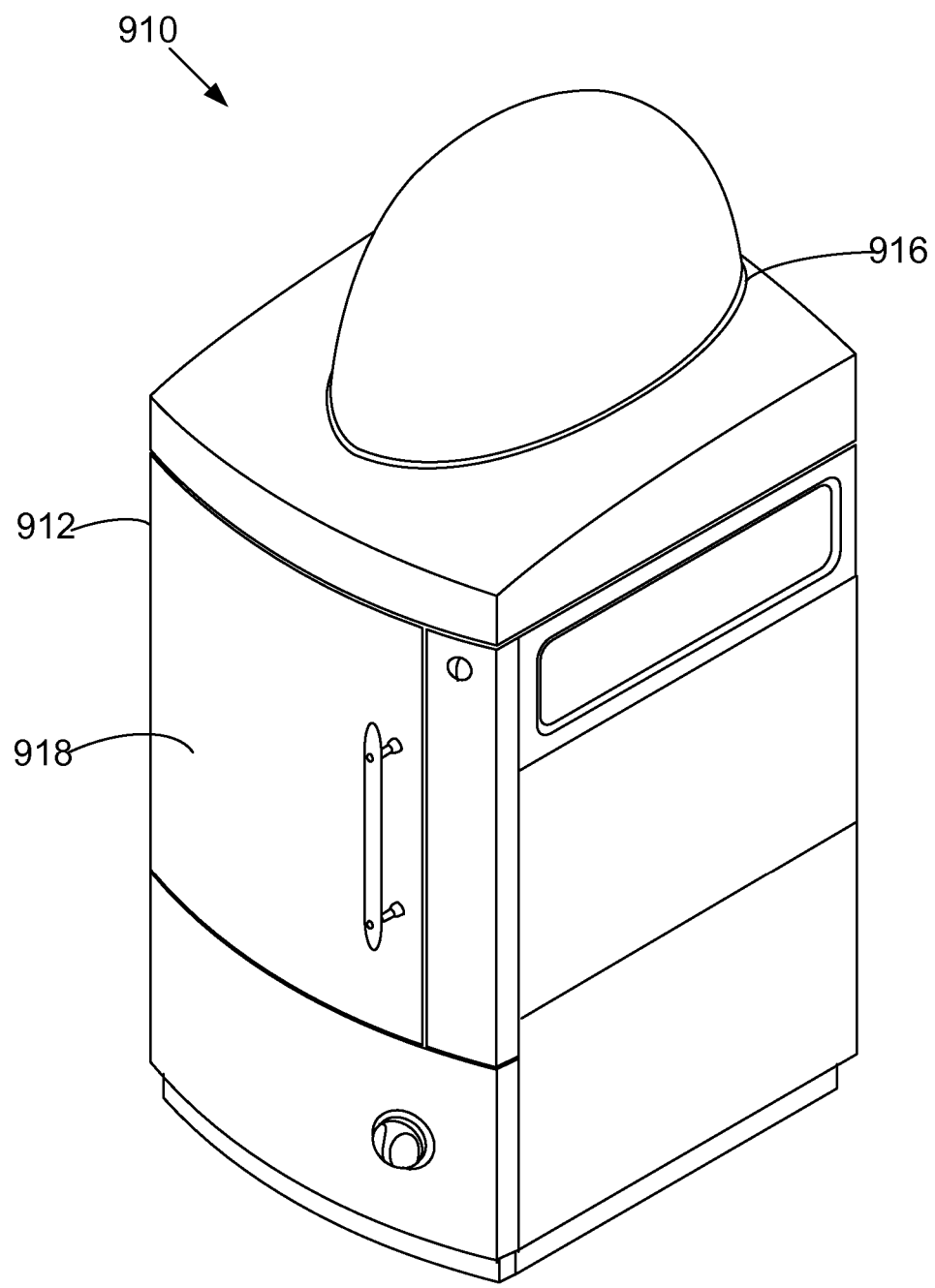
FIGS. 9A and 9B illustrate an imaging system in accordance with one embodiment of the present invention.
Figure 9B:
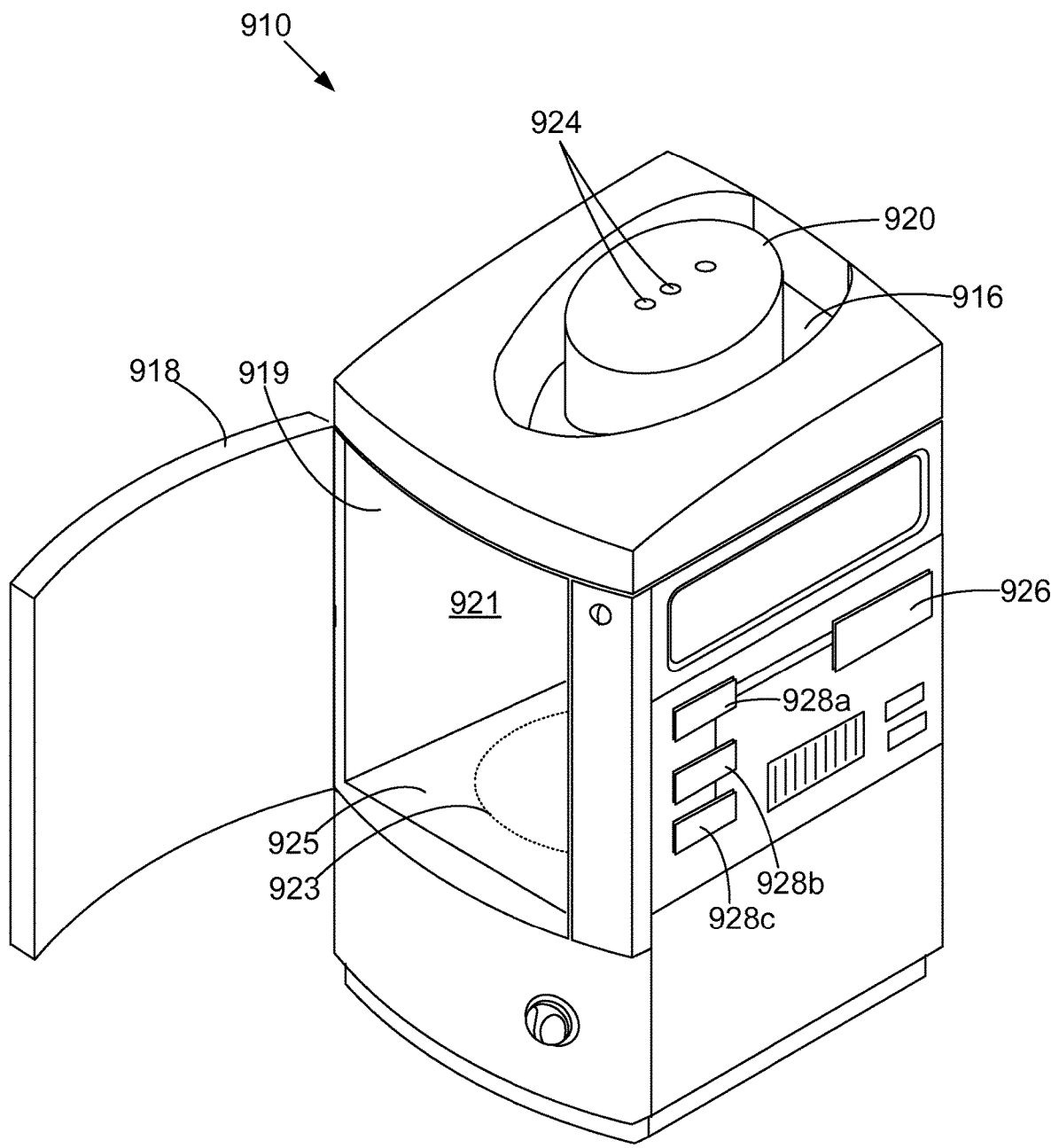

FIGS. 9A and 9B illustrate an imaging system in accordance with one embodiment of the present invention. Imaging system 910 comprises an imaging box 912 having a door 918 and inner walls 919 (FIG. 9B) that define an interior cavity 921 that is adapted to receive a specimen in which low intensity light is to be detected. Imaging box 912 is suitable for imaging including the capture of low intensity light on the order of individual photons, for example. Imaging box 912 is often referred to as "light-tight". That is, box 912 seals out essentially all of the external light from the ambient room from entering the box 912, and may include one or more seals that prevent light passage into the box when door 918 is closed. In a specific embodiment, door 918 comprises one or more light-tight features such as a double baffle seal, while the remainder of chamber 921 is configured to minimize any penetration of light into cavity 921.

A specimen may be placed within box 912 for imaging by opening door 918, inserting the mouse in chamber 921, and closing door 918. Suitable imaging systems are available from Xenogen Corporation from Alameda, Calif., and include the IVIS® Spectrum, IVIS® 3D Series, IVIS® 200 Series, IVIS® 100 Series, and IVIS® Lumina. Further description of a suitable imaging box 912 is provided in commonly owned U.S. Pat. No. 7,113,217, entitled "3-D IMAGING APPARATUS FOR IN-VIVO REPRESENTATIONS", issued 26 Sep. 2006 by David Nilson et al., which patent is incorporated herein by reference in its entirety for all purposes. Although imaging system 910 is shown with a single cabinet design, other embodiments of the present invention include a disparate imaging box 912 and desktop computer that includes processing system 928 and a dedicated display.

Imaging box 912 includes an upper housing 916 adapted to receive a camera 920 (FIG. 14B). A high sensitivity camera 920, e.g., an intensified or a charge-coupled device (CCD) camera, is mounted on top of upper housing 916 and positioned above imaging box 912. CCD camera 920 is capable of capturing luminescent, fluorescent, structured light and photographic (i.e., reflection based images) images of a living sample or phantom device placed within imaging box 912. One suitable camera includes a Spectral Instruments 620 Series as provided by Spectral Instruments of Tucson, Ariz. CCD camera 920 is cooled by a suitable source thermoelectric chiller. Other methods, such as liquid nitrogen, may be used to cool camera 920. Camera may also be side-mounted, or attached to a moving chassis that moves the camera in cavity 921.

Imaging system 910 may also comprise a lens (not shown) that collects light from the specimen or phantom device and provides the light to the camera 920. A stage 925 forms the bottom floor of imaging chamber 921 and includes motors and controls that allow stage 925 to move up and down to vary the field of view 923 for camera 920. A multiple position filter wheel may also be provided to enable spectral imaging capability. Imaging box 912 may also include one or more light emitting diodes on the top portion of chamber 921 to illuminate a sample during photographic image capture. Other features may include a gas anesthesia system to keep the mouse anesthetized and/or a heated shelf to maintain an animal's body temperature during image capture and anesthesia.

Imaging box 912 also includes one or more fluorescent excitation light sources. In one embodiment, box 912 includes a trans-illumination device and an epi-illumination device. As mentioned above with respect to FIG. 8, the trans-illumination device is configured to direct light into a first surface of the mouse, where diffused light exits a second surface of the mouse. An epi-illumination type device may be configured direct light onto a third surface of the specimen, where the diffused light exits the third surface of the mouse. Further description of fluorescent excitation light sources is provided in U.S. patent application Ser. No. 11/434,606, entitled "A DUAL ILLUMINATION SYSTEM FOR AN IMAGING APPARATUS AND METHOD", filed 15 May 2006 by David Nison et al., which is incorporated herein by reference in its entirety for all purposes.

A structured light source is included in imaging box. The structured light source includes a mechanism for transmitting a set of lines onto the object from an angle. The lines are displaced, or phase shifted relative to a stage, when they encounter an object with finite height, such as a mouse. This phase shift provides structured light information for the object. Camera 920 then captures the structured light information. Using software that employs a structured light analysis, surface topography data for the object (over its entire surface or a portion) is determined from the phase shift of the lines.

FIG. 9B shows system 910 with the removal of a side panel for imaging box 912 to illustrate various electronics and processing components included in system 910. Imaging system 910 comprises image processing unit 926 and processing system 928. Image processing unit 926 optionally interfaces between camera 920 and processing system 928 and may assist with image data collection and video data processing. Processing system 928, which may be of any suitable type, comprises hardware including a processor 928a and one or more memory components such as random-access memory (RAM) 928b and read-only memory (ROM) 928c.

Processor 928a (also referred to as a central processing unit, or CPU) couples to storage devices including memory 928b and 928c. ROM 928c serves to transfer data and instructions uni-directionally to the CPU, while RAM 28b typically transfers data and instructions in a bi-directional manner. A fixed disk is also coupled bi-directionally to processor 928a; it provides additional data storage capacity and may also include any of the computer-readable media described below. The fixed disk may be used to store software, programs, imaging data and the like and is typically a secondary storage medium (such as a hard disk).

Processor 928a communicates with various components in imaging box 912. To provide communication with, and control of, one or more system 910 components, processing system 928 employs software stored in memory 928c that is configured to permit communication with and/or control of components in imaging box 912. For example, processing system 28 may include hardware and software configured to control camera 920. The processing hardware and software may include an I/O card, control logic for controlling camera 920. Components controlled by computer 928 may also include motors responsible for camera 920 focus, motors responsible for position control of a platform supporting the sample, a motor responsible for position control of a filter lens, f-stop, etc.

Processing system 928 may also interface with an external visual display (such as computer monitor) and input devices such as a keyboard and mouse. A graphical user interface that facilitates user interaction with imaging system 910 may also be stored on system 928, output on the visual display and receive user input from the keyboard and mouse. The graphical user interface allows a user to view imaging results and also acts an interface to control the imaging system 910. One suitable imaging software includes "LivingImage" as provided by Xenogen Corporation of Alameda, Calif.

Processing system 928 may comprise software, hardware or a combination thereof. System 928 may also include additional imaging hardware and software, tomographic reconstruction software that implements process flows and methods described above, and image processing logic and instructions for processing information obtained by camera 920. For example, stored instructions run by processor 28a may include instructions for i) receiving image data corresponding to light emitted from a mouse as described herein, ii) determining optical properties, (iii) building a 3-D digital representation of a fluorescent probe internal to a mouse using data included in an image, and iv) outputting results of a tomographic reconstruction on a display such as a video monitor.

Imaging system 910 employs a quantitative model that estimates the diffusion of photons in tissue. In one embodiment, the model processes in vivo image data and in order to determine optical properties based on a calibrated light source and/or use the determined optical properties to spatially resolve a 3D representation of the size, shape, and location of an internal, noncalibrated light emitting source. Regardless of the imaging and computing system configuration, imaging apparatus 910 may employ one or more memories or memory modules configured to store program instructions for determining optical properties, obtaining a 3D representation of a probe located inside a sample, and other functions of the present invention described herein. Such memory or memories may also be configured to store data structures, imaging data, or other specific non-program information described herein. Because such information and program instructions may be employed to implement the systems/methods described herein, the present invention relates to machine-readable media that include program instructions, state information, etc. for performing various operations described herein. Examples of tangible machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter. The invention may also be embodied in a carrier wave traveling over an appropriate medium such as airwaves, optical lines, electric lines, etc.

Although the foregoing invention has been described in some detail for purposes of clarity of understanding, it will be apparent that certain changes and modifications may be practiced within the scope of the appended claims. Therefore, the present embodiments are to be considered as illustrative and not restrictive and the invention is not to be limited to the details given herein, but may be modified within the scope and equivalents of the appended claims.

What is claimed is:

1. A method of determining optical properties in an animal, the method comprising:
    measuring a surface topography of a second surface of the animal, wherein the second surface has a complex three-dimensional profile;
    conducting tomographic imaging on the animal separately from said measuring a surface topography, the tomographic imaging comprising:
        illuminating a first surface of the animal opposite the second surface with light from only a single light source, having a first wavelength and a known illumination power, sequentially at a plurality of specific illumination positions on the first surface of the animal; and
        for each specific illumination position of the single light source, obtaining light emission measurements from the second surface, wherein the light emission measurements are obtained for a plurality of surface positions of the second surface;
    determining a measured photon density distribution just inside the second surface of the animal from the light emission measurements and the surface topography using a model for photon propagation at a tissue-air interface; and
    for each specific illumination position of the single light source, determining a reduced scattering coefficient $\mu_s'$ and an absorption coefficient $\mu_A$ for the animal based on the specific illumination position of the single light source, the first wavelength of the single light source, the known illumination power of the single light source, the measured surface topography of the second surface, and the light emission measurements for each specific illumination position, wherein the optical properties for the plurality of specific illumination positions of the single light source are individually determined for each specific illumination position of the single light source,
    wherein determining the reduced scattering coefficient $\mu_s'$ and the absorption coefficient $\mu_A$ comprises:
        using a forward model of photon propagation within the animal that generates, at each iteration, an updated calculated photon density distribution just inside the second surface of the animal;
        during each iteration of the forward model, updating values for $\mu_s'$ and $\mu_A$ to generate the updated calculated photon density distribution such that the updated values for $\mu_s'$ and $\mu_A$ yield a best fit between the updated calculated photon density distribution and the measured photon density distribution; and
        performing successive iterations of the forward model until the updated calculated photon density distribution is within a predetermined specification of the measured photon density distribution just inside the second surface of the animal.

2. The method as recited in claim 1, further comprising repeating said conducting and determining steps for a second wavelength of the single light source that differs from the first wavelength.

3. The method as recited in claim 1, wherein the light source is modeled as a point source located a distance $1.2/\mu_s'$ from the first surface and three additional image sources in the forward model.

4. The method as recited in claim 1, wherein the model for photon propagation at the tissue-air interface is a diffusion model.

5. The method as recited in claim 1, wherein $\mu_s'$ and $\mu_A$ are varied in the forward model of photon propagation until $\chi^2$ is minimized, wherein $$\chi^2 = \sum_i (y_i - L_i)^2 w_i,$$

and wherein
    $L_i$ is the measured photon density for each position just inside the second surface,
    $y_i$ is a calculated photon density for each position just inside the second surface, and
    $w_i$ is a weighting function for each position just inside the second surface.

6. The method as recited in claim 5, wherein:
    $w_i$ is zero if the position just inside the second surface is within a threshold distance of an edge of a simulated surface mesh; and
    otherwise $w_i$ is $1/L_i$.

7. The method as recited in claim 1, further comprising calibrating the single light source to measure the illumination power of the single light source.

8. The method as recited in claim 1, further comprising using the determined reduced scattering coefficient $\mu_s'$ and absorption coefficient $\mu_A$ to correct optical properties derived from a Monte Carlo or Finite Element Model (FEM) simulation of heterogeneous tissue properties so that the simulation can be used to determine an internal light source distribution for the animal, wherein the uncorrected optical properties were derived from a simulation for a different animal.

9. An imaging apparatus for determining optical properties of a animal, comprising:

one or more light sources that are positionable at a plurality of different illumination positions relative to a first surface of the animal;

a detector positioned to detect light emission measurements from a second surface of the animal that is opposite to the first surface; and a processor, wherein the processor is configured to:

measure a surface topography of the second surface of the animal, wherein the second surface has a complex three-dimensional profile;

conduct tomographic imaging on the animal separately from said measuring a surface topography, the tomographic imaging comprising:

illuminating the first surface of the animal with light from only a single one of the one or more light sources having a first wavelength and a known illumination power, sequentially at a plurality of specific illumination positions on the first surface; and for each specific illumination position of the single light source, obtaining light emission measurements from the second surface for a plurality of surface positions of the second surface;

determine a measured photon density distribution just inside the second surface of the animal from the light emission measurements and the surface topography using a model for photon propagation at a tissue-air interface; and for each specific illumination position of the single light source, determine a reduced scattering coefficient $\mu_s'$ and an absorption coefficient $\mu_A$ for the animal based on the specific illumination position of the single light source, the first wavelength of the single light source, the known illumination power of the single light source, the measured surface topography of the second surface, and the light emission measurements for each specific illumination position, wherein the optical properties for the plurality of specific illumination positions of the single light source are individually determined for each specific illumination position of the single light source, wherein determining the reduced scattering coefficient $\mu_s'$ and the absorption coefficient $\mu_A$ comprises:

using a forward model of photon propagation within the animal that generates, at each iteration, an updated calculated photon density distribution just inside the second surface of the animal;

during each iteration of the forward model, updating values for $\mu_s'$ and $\mu_A$ to generate the updated calculated photon density distribution such that the updated values for $\mu_s'$ and $\mu_A$ yield a best fit between the updated calculated photon density distribution and the measured photon density distribution; and performing successive iterations of the forward model until the updated calculated photon density distribution is within a predetermined specification of the measured photon density distribution just inside the second surface of the animal.

10. The imaging apparatus as recited in claim 9, wherein the processor is further configured to determine the reduced scattering coefficient $\mu_s'$ and the absorption coefficient $\mu_A$ for a second wavelength of the single light source that differs from the first wavelength.

11. The imaging apparatus as recited in claim 9, wherein the light source is modeled as a point source located a distance $1.2/\mu_s'$ from the first surface and three additional image sources in the forward model.

12. The imaging apparatus as recited in claim 9, wherein the model for photon propagation at the tissue-air interface is a diffusion model.

13. The imaging apparatus as recited in claim 9, wherein the processor is configured to vary $\mu_s'$ and $\mu_A$ in the forward model of photon propagation until $\chi^2$ is minimized, wherein $$\chi^2 = \sum_i (y_i - L_i)^2 w_i,$$

and wherein $L_i$ is the measured photon density for each position just inside the second surface, $y_i$ is a calculated photon density for each position just inside the second surface, and $w_i$ is a weighting function for each position just inside the second surface.

14. The imaging apparatus as recited in claim 13, wherein:

$w_i$ is zero if the position just inside the second surface is within a threshold distance of an edge of a simulated surface mesh; and otherwise $w_i$ is $1/L_i$.

15. The imaging apparatus as recited in claim 9, wherein the processor is further configured to calibrate the single light source so as to measure the illumination power of the single light source.

16. The imaging apparatus as recited in claim 9, wherein the processor is further configured to use the determined reduced scattering coefficient $\mu_s'$ and absorption coefficient $\mu_A$ to correct optical properties derived from a Monte Carlo or Finite Element Model (FEM) simulation so that the simulation can be used to determine an internal light source distribution for the animal, wherein the uncorrected optical properties were derived from a simulation for a different animal.

17. A non-transitory and tangible computer readable storage medium having computer program instructions stored thereon that, when read by a processor, causes the processor to:

measure a surface topography of a second surface of an animal, wherein the second surface has a complex three-dimensional profile;

conduct tomographic imaging on the animal separately from said measuring a surface topography, the tomographic imaging comprising:

illuminating a first surface of the animal opposite to the second surface with light from a single light source having a first wavelength and a known illumination power, sequentially at a plurality of specific illumination positions on the first surface; and for each specific illumination position of the single light source, obtaining light emission measurements from the second surface for a plurality of surface positions of the second surface;

determine a measured photon density distribution just inside the second surface of the animal from the light emission measurements and the surface topography using a model for photon propagation at a tissue-air interface; and for each specific illumination position of the single light source, determine a reduced scattering coefficient $\mu_s'$ and an absorption coefficient $\mu_A$ for the animal based on the specific illumination position of the single light source, the first wavelength of the single light source, the known illumination power of the single light source, the measured surface topography of the second surface, and the light emission measurements for each specific illumination position, wherein the optical properties for the plurality of specific illumination positions of the single light source are individually determined for each specific illumination position of the single light source, wherein determining the reduced scattering coefficient $\mu_s'$ and the absorption coefficient $\mu_A$ comprises:

using a forward model of photon propagation within the animal that generates, at each iteration, an updated calculated photon density distribution just inside the second surface of the animal;

during each iteration of the forward model, updating values for $\mu_s'$ and $\mu_A$ to generate the updated calculated photon density distribution such that the updated values for $\mu_s'$ and $\mu_A$ yield a best fit between the updated calculated photon density distribution and the measured photon density distribution; and performing successive iterations of the forward model until the updated calculated photon density distribution is within a predetermined specification of the measured photon density distribution just inside the second surface of the animal.

* * * * *